US006515202B1

(12) United States Patent
Crane et al.

(10) Patent No.: US 6,515,202 B1
(45) Date of Patent: Feb. 4, 2003

(54) POLYNUCLEOTIDES ENCODING MONOCOT 12-OXO-PHYTODIENOATE REDUCTASES AND METHODS OF USE

(75) Inventors: Virginia C. Crane, Des Moines, IA (US); Jon Duvick, Des Moines, IA (US); Yogesh K. Sharma, Maryland Heights, MO (US); Oswald R. Crasta, Clinton, CT (US); Otto Folkerts, Guilford, CT (US)

(73) Assignees: Pioneer Hi-Bred International, Inc., Des Moines, IA (US); CuraGen Corporation, New Haven, CT (US)

( * ) Notice: Subject to any disclaimer, the term of this patent is extended or adjusted under 35 U.S.C. 154(b) by 0 days.

(21) Appl. No.: 09/573,906

(22) Filed: May 18, 2000

Related U.S. Application Data

(60) Provisional application No. 60/134,911, filed on May 19, 1999, and provisional application No. 60/134,808, filed on May 19, 1999.

(51) Int. Cl.[7] .............................. A01H 5/00; C12N 5/04; C12N 9/02; C12N 15/29; C12N 15/82; C12N 15/53

(52) U.S. Cl. ........................ 800/279; 800/298; 800/287; 800/286; 800/301; 800/302; 800/312; 800/306; 800/322; 800/314; 800/317.2; 800/320; 800/320.2; 800/320.1; 800/320.3; 435/418; 435/419; 435/468; 435/189; 536/23.2; 536/23.6; 536/24.5

(58) Field of Search .............................. 536/23.2, 23.6, 536/24.5; 800/278, 279, 289, 287, 290, 320.1, 320, 320.2, 306, 320.3, 322, 312, 317.2, 314, 298, 286, 301, 302; 435/468, 418, 419, 189

(56) References Cited

PUBLICATIONS

Blechert, S., et al., "The Octadecanoic Pathway: Signal Molecules for the Regulation of Secondary Pathways," *Proc. Natl. Acad. Sci. USA,* May 1995, pp. 4099–4105, vol. 92, The National Academy of Sciences, USA.
Creelman, R.A., and J.E. Mullet, "Biosynthesis and Action of Jasmonates in Plants," *Annu. Rev. Plant Physiol. Plant Mol. Biol.,* 1997, pp. 355–381, vol. 48.
Dong, X., "SA, JA, Ethylene, and Disease Resistance in Plants," *Current Opinion of Plant Biology,* 1998, pp. 316–323, vol. 1.
McConn, M., et al., "Jasmonate is Essential for Insect Defense in Arabidopsis," *Proc. Natl. Acad. Sci. USA,* May 1997, pp. 5473–5477, vol. 94, The National Academy of Sciences, USA.
Parchmann, S., et al., "Induction of 12–Oxo–Phytodienoic Acid in Wounded Plants and Elicited Plant Cell Cultures," *Plant Physiol.,* 1997, pp. 1057–1064, vol. 115.

Schaller, F., et al., "12–Oxophytodienoate–10, 11–Reductase: Occurrence of Two Isoenzymes of Different Specificity Against Stereoisomers of 12–Oxophytodienoic Acid," *Plant Physiol.,* 1998, pp. 1345–1351, vol. 118.
Schweizer, P., et al, "Induced Systemic Resistance in Wounded Rice Plants," *The Plant Journal,* 1998, pp. 475–481, vol. 14(4), Blackwell Science Ltd., USA.
Staswick, P., et al., "Jasmonate Signaling Mutants of Arabidopsis Are Susceptible to the Soil Fungus *Phythium irrregulare*", *The Plant Journal,* 1998 pp. 747–754, vol. 15(6), Blackwell Science Ltd., USA.
Vijayan, P., et al., "A Role for Jasmonate in Pathogen Defense of *Arabidopsis,"* *Proc. Natl. Acad. Sci. USA,* Jun. 1998, pp. 7209–7214, vol. 95, The National Academy of Sciences, USA.
Wasternack, C., and B. Parthier, "Jasmonate–Signalled Plant Gene Expression," *Trends in Plant Science,* Aug. 1997, pp. 302–307, vol. 2(8), Elsevier Science Ltd., USA.
Weber, H., et al., "Dinor–Oxo–Phytodienoic Acid: A New Hexadecanoid Signal in the Jasmonate Family," *Proc. Natl. Acad. Sci. USA,* Sep. 1997, pp. 10473–10478, vol. 94, The National Academy of Sciences, USA.
Yamamoto et al. Rice cDNA from mature leaf LOCUS AU057040 711 Apr. 29, 1999.
Schaller et al. Oxophytodienoate reductase 3 (OPR3) is the isoenzyme involved in jasmonate biosynthesis Planta (2000) 210:979–984 May No:6.
Stintzi et al. The arabidopsis male–sterile mutant, opr3, lacks the 12–oxophytodienoic acid reductase required for jasmonate synthesis Sep. 12, 2000 vol. 97 No. 19.
Biesgen et al. Structure and regulation of OPR1 and OPR2, two closely related genes encoding 12–oxophytodienoic acid–10, 11–reductases from arabidopsis thaliana Planta 1999 208: 155–165.
Schaller et al. Molecular cloning and characterization of 12–oxophytodienoate reductase, an enzyme ao the octadecanoid signaling pathway from arabidopsis thaliana Journal of Biological Chemistry 1997 vol. 272,No.44, Oct. 31 pp. 28066–28072.*
Hill et al. Functional analysis of conserved histidines in ADP–Glucose pyrophosphorylase from *escherichia coli* Biochemical and Biophysical Research communications 244, 573–577, 1998 article No. RC988301.*
Broun et al. Catalytic plasticity of fatty acid modification enzymes underlying chemical diversity of plant lipids Science vol. 282 Nov. 12, 1998.*

(List continued on next page.)

*Primary Examiner*—David T. Fox
*Assistant Examiner*—Anne Kubelik
(74) *Attorney, Agent, or Firm*—Alston & Bird LLP

(57) ABSTRACT

The invention relates to the genetic manipulation of plants, particularly to the expression of genes involved in oxylipin metabolism in plants. Nucleotide sequences encoding homologues of Old Yellow Enzyme, and inducible promoters and proteins thereof, are provided. The sequences find use in modifying oxylipin metabolism in plants, increasing the resistance of plants to stress, regulating gene expression in plants, and in the production of oxylipins in plants.

24 Claims, 4 Drawing Sheets

OTHER PUBLICATIONS

Bowie et al. Deciphering the message in protein sequences: tolerance to amino acid substitutions Science, vol. 247.*

Lazar et al. Transforming growth factor @: mutation if aspartic acid 47 and leucine 47 results in defferent biological activities Molecular and Cellular Biology, Mar. 1988, p. 1247–1252.*

Iuchi et al. Novel drought–inducble genes in the highly drought–tolerant cowpea:cloning of cDNA's and analysis of the expression of the corresponding genes Plant Cell Physical 37(8): 1073–1082 1996.*

Stelmach et al., A Novel Class of Oxlipins, sn 1–O–(12–Oxophytodienoyl)–sn2–O–(hexadecatrienoyl)..., Apr. 2001, The Journal of Biological Chemisty, vol. 27, No. 16, pp. 12832–12838.*

Brasg et al., Lipoxgenases: Occurrence, Functions, Catalysis, and Acquistion of Substrate, 1999, The Journal of Biological Chemistry, vol. 274, No. 34, pp. 23679–23682.*

Sanders et al., The Arabidopsis DELAYED DEHISCENCE1 Gene Encodes an Enzyme in the Jasmonic Acid Synthesis Pathway, 2000, The Plant Cell, vol. 12, pp. 1041–1061.*

* cited by examiner 6h   1d
-  +  -  +

ZmOYE1

Actin

SEQUENCE LISTING

```
<160> NUMBER OF SEQ ID NOS:  9

<210> SEQ ID NO 1
<211> LENGTH: 1465
<212> TYPE: DNA
<213> ORGANISM: Zea mays
<220> FEATURE:
<221> NAME/KEY: CDS
<222> LOCATION: (101)..(1225)

<400> SEQUENCE: 1
aagcagagcg agaaaccgag caaattaagc tagtaagagc agagagctgc aagtgacctg         60
cggtgttgca tcacatctgc agcagcagca cgccggcaag atg gtg cag caa gcc        115
                                              Met Val Gln Gln Ala
                                                1               5 gcg aag gag gtg atc ccg ctg ctg acg cct tac aag atg ggg cag ttc        163
Ala Lys Glu Val Ile Pro Leu Leu Thr Pro Tyr Lys Met Gly Gln Phe
                10                  15                  20 gag ctc tct cac cgg gtg gtg ctg gcg ccg ctg acg agg tgc cgc tcc        211
Glu Leu Ser His Arg Val Val Leu Ala Pro Leu Thr Arg Cys Arg Ser
            25                  30                  35 tac ggc aac gtg ccg cag cca cac gcc gcc gtg tac tac tcc cag cgc        259
Tyr Gly Asn Val Pro Gln Pro His Ala Ala Val Tyr Tyr Ser Gln Arg
        40                  45                  50 gcc acc agg ggt ggc ctg ctc atc gcg gag gcc acg ggg gtg tcg gcc        307
Ala Thr Arg Gly Gly Leu Leu Ile Ala Glu Ala Thr Gly Val Ser Ala
    55                  60                  65 acc gcg cag ggg tac ccg gag act cct ggc atc tgg acg cag gag cag        355
Thr Ala Gln Gly Tyr Pro Glu Thr Pro Gly Ile Trp Thr Gln Glu Gln
70                  75                  80                  85
```

-continued

| | |
|---|---|
| gtc gag gcg tgg aag ccc atc gtc gac gcc gtc cac cgc aag ggc gcc<br>Val Glu Ala Trp Lys Pro Ile Val Asp Ala Val His Arg Lys Gly Ala<br>                                90                                    95                                  100 | 403 |
| atc ttc gtc tgc cag atc tgg cat gtg ggc agg gtc tcc acc aac gag<br>Ile Phe Val Cys Gln Ile Trp His Val Gly Arg Val Ser Thr Asn Glu<br>                         105                                 110                               115 | 451 |
| ctc cag ccg aac ggc gat gcg cct atc tcg agc acg gac aag cag atc<br>Leu Gln Pro Asn Gly Asp Ala Pro Ile Ser Ser Thr Asp Lys Gln Ile<br>                   120                               125                               130 | 499 |
| tcc ccc gac gcc gag tcc gga acg gcg tac tcg aag ccg cgc cgg ctg<br>Ser Pro Asp Ala Glu Ser Gly Thr Ala Tyr Ser Lys Pro Arg Arg Leu<br>       135                                 140                               145 | 547 |
| cgg acc gac gag gtc ccc ggg atc gtc gac gac ttc agg cgg gcc gca<br>Arg Thr Asp Glu Val Pro Gly Ile Val Asp Asp Phe Arg Arg Ala Ala<br>150                            155                                 160                        165 | 595 |
| cgg aac gcg atc cag gct ggc ttc gac gcc gtc gag atc cac ggc gcg<br>Arg Asn Ala Ile Gln Ala Gly Phe Asp Ala Val Glu Ile His Gly Ala<br>                   170                               175                               180 | 643 |
| cac ggg tat ctc ctg gag cag ttc atg aag gac agc tgc aac gac cgc<br>His Gly Tyr Leu Leu Glu Gln Phe Met Lys Asp Ser Cys Asn Asp Arg<br>       185                                 190                               195 | 691 |
| acg gac cag tac ggc ggc agc ctg gag aac cgg tgc cgt ctc gcc gtg<br>Thr Asp Gln Tyr Gly Gly Ser Leu Glu Asn Arg Cys Arg Leu Ala Val<br>                   200                               205                               210 | 739 |
| gag gtc gtg gac gcc gtc gtc cgc gag gtg ggc gcg cgc cgc gtc ggc<br>Glu Val Val Asp Ala Val Val Arg Glu Val Gly Ala Arg Arg Val Gly<br>       215                                 220                               225 | 787 |
| atc agg ctg tcg ccc ttc gtc gac ttc gtg gac tgc gtc gac tcg gac<br>Ile Arg Leu Ser Pro Phe Val Asp Phe Val Asp Cys Val Asp Ser Asp<br>230                            235                                 240                        245 | 835 |
| ccg gtg gcg ctc ggc cac tac atg gtg cag cag ctc aac agg cat agc<br>Pro Val Ala Leu Gly His Tyr Met Val Gln Gln Leu Asn Arg His Ser<br>                   250                               255                               260 | 883 |
| ggc ttg ctc tac tgc cac atg gta gag ccc cgc atg gct acc gtc gac<br>Gly Leu Leu Tyr Cys His Met Val Glu Pro Arg Met Ala Thr Val Asp<br>                 265                               270                               275 | 931 |
| ggg cgc agg cag atc cct cac ggg ctc ttg ccg ttc cga aag gcg ttc<br>Gly Arg Arg Gln Ile Pro His Gly Leu Leu Pro Phe Arg Lys Ala Phe<br>               280                               285                               290 | 979 |
| cat gga acg ttc atc gcc gcc ggt ggg tac gat cgg gag gat ggc aac<br>His Gly Thr Phe Ile Ala Ala Gly Gly Tyr Asp Arg Glu Asp Gly Asn<br>       295                                 300                               305 | 1027 |
| aag gtg gtg gca gaa ggg tat gct gac ctc gtc gcg tat ggg agg ctg<br>Lys Val Val Ala Glu Gly Tyr Ala Asp Leu Val Ala Tyr Gly Arg Leu<br>310                            315                                 320                        325 | 1075 |
| ttc ttg gct aac cca gac cta cct agg agg ttc gag ctg gat gtg gca<br>Phe Leu Ala Asn Pro Asp Leu Pro Arg Arg Phe Glu Leu Asp Val Ala<br>                   330                               335                               340 | 1123 |
| ctc aac aaa tac gac cgc tcc acc ttc tac acg caa gat cct att gtt<br>Leu Asn Lys Tyr Asp Arg Ser Thr Phe Tyr Thr Gln Asp Pro Ile Val<br>                 345                               350                               355 | 1171 |
| ggc tac aca gat tac cct ttc ttt gaa gaa gat ggc aag aat gag gag<br>Gly Tyr Thr Asp Tyr Pro Phe Phe Glu Glu Asp Gly Lys Asn Glu Glu<br>               360                               365                             370 | 1219 |
| tca gtc tgatcacaac taataatgtg gagggttcat caagtttgag ttcatcatta<br>Ser Val<br>     375 | 1275 |
| tttccaccat ttattattat tggccattat ggcggagtca ttgcgtcgtg ttgtttcatt | 1335 |
| atgtactagt gtaaagtgaa ataaatcatg tactagtgtg aagtgaaata aatctagcta | 1395 |

-continued

```
tttcgtaaaa ttattataaa ataaattatt acttttttct aaaaaaaaaa aaaaaaaaaa    1455
aaaaaaaaaa                                                           1465
```

<210> SEQ ID NO 2
<211> LENGTH: 375
<212> TYPE: PRT
<213> ORGANISM: Zea mays

<400> SEQUENCE: 2

```
Met Val Gln Gln Ala Ala Lys Glu Val Ile Pro Leu Leu Thr Pro Tyr
 1               5                  10                  15

Lys Met Gly Gln Phe Glu Leu Ser His Arg Val Val Leu Ala Pro Leu
             20                  25                  30

Thr Arg Cys Arg Ser Tyr Gly Asn Val Pro Gln Pro His Ala Ala Val
         35                  40                  45

Tyr Tyr Ser Gln Arg Ala Thr Arg Gly Gly Leu Leu Ile Ala Glu Ala
     50                  55                  60

Thr Gly Val Ser Ala Thr Ala Gln Gly Tyr Pro Glu Thr Pro Gly Ile
 65                  70                  75                  80

Trp Thr Gln Glu Gln Val Glu Ala Trp Lys Pro Ile Val Asp Ala Val
                 85                  90                  95

His Arg Lys Gly Ala Ile Phe Val Cys Gln Ile Trp His Val Gly Arg
            100                 105                 110

Val Ser Thr Asn Glu Leu Gln Pro Asn Gly Asp Ala Pro Ile Ser Ser
        115                 120                 125

Thr Asp Lys Gln Ile Ser Pro Asp Ala Glu Ser Gly Thr Ala Tyr Ser
    130                 135                 140

Lys Pro Arg Arg Leu Arg Thr Asp Glu Val Pro Gly Ile Val Asp Asp
145                 150                 155                 160

Phe Arg Arg Ala Ala Arg Asn Ala Ile Gln Ala Gly Phe Asp Ala Val
                165                 170                 175

Glu Ile His Gly Ala His Gly Tyr Leu Leu Glu Gln Phe Met Lys Asp
            180                 185                 190

Ser Cys Asn Asp Arg Thr Asp Gln Tyr Gly Gly Ser Leu Glu Asn Arg
        195                 200                 205

Cys Arg Leu Ala Val Glu Val Val Asp Ala Val Val Arg Glu Val Gly
    210                 215                 220

Ala Arg Arg Val Gly Ile Arg Leu Ser Pro Phe Val Asp Phe Val Asp
225                 230                 235                 240

Cys Val Asp Ser Asp Pro Val Ala Leu Gly His Tyr Met Val Gln Gln
                245                 250                 255

Leu Asn Arg His Ser Gly Leu Leu Tyr Cys His Met Val Glu Pro Arg
            260                 265                 270

Met Ala Thr Val Asp Gly Arg Arg Gln Ile Pro His Gly Leu Leu Pro
        275                 280                 285

Phe Arg Lys Ala Phe His Gly Thr Phe Ile Ala Ala Gly Gly Tyr Asp
    290                 295                 300

Arg Glu Asp Gly Asn Lys Val Val Ala Glu Gly Tyr Ala Asp Leu Val
305                 310                 315                 320

Ala Tyr Gly Arg Leu Phe Leu Ala Asn Pro Asp Leu Pro Arg Arg Phe
                325                 330                 335

Glu Leu Asp Val Ala Leu Asn Lys Tyr Asp Arg Ser Thr Phe Tyr Thr
            340                 345                 350
```

```
Gln Asp Pro Ile Val Gly Tyr Thr Asp Tyr Pro Phe Phe Glu Glu Asp
        355                 360                 365

Gly Lys Asn Glu Glu Ser Val
    370                 375

<210> SEQ ID NO 3
<211> LENGTH: 1409
<212> TYPE: DNA
<213> ORGANISM: Zea mays
<220> FEATURE:
<221> NAME/KEY: CDS
<222> LOCATION: (86)..(1210)

<400> SEQUENCE: 3
agcaaagcga gcaacagagc agaagcaaag cgcagagcta gcaagtgacc gaccgagagc         60
aaataggcat ggcaacgcag gcaag atg gtg cag caa gcc gcg aag gag gtg         112
                            Met Val Gln Gln Ala Ala Lys Glu Val
                              1               5 atc ccg ctg ctg acg cct tac aag atg ggg cag ttc gag ctc tct cac         160
Ile Pro Leu Leu Thr Pro Tyr Lys Met Gly Gln Phe Glu Leu Ser His
 10              15                  20                  25 cgg gtg gtg ctg gcg ccg ctg acg agg tgc cgc tcc tac ggc aac gtg         208
Arg Val Val Leu Ala Pro Leu Thr Arg Cys Arg Ser Tyr Gly Asn Val
                 30                  35                  40 ccg cag cca cac gcc gcc gtg tac tac tcg cag cgc gcc acc agg ggt         256
Pro Gln Pro His Ala Ala Val Tyr Tyr Ser Gln Arg Ala Thr Arg Gly
             45                  50                  55 ggc ctg ctc atc gcg gag gcc acg ggg gtg tcg gcc acc gcg cag ggg         304
Gly Leu Leu Ile Ala Glu Ala Thr Gly Val Ser Ala Thr Ala Gln Gly
         60                  65                  70 ttc ccg gag tct cct ggc atc tgg acg cag gag cag gtc gag gcg tgg         352
Phe Pro Glu Ser Pro Gly Ile Trp Thr Gln Glu Gln Val Glu Ala Trp
     75                  80                  85 aag ccc atc gtc gac gcc gtc cac cgc aag ggc gcc atc ttc gtc tgc         400
Lys Pro Ile Val Asp Ala Val His Arg Lys Gly Ala Ile Phe Val Cys
 90                  95                 100                 105 cag atc tgg cat gtg ggc agg gtc tcc acc aac gag ctc cag ccc aac         448
Gln Ile Trp His Val Gly Arg Val Ser Thr Asn Glu Leu Gln Pro Asn
                110                 115                 120 ggc gac gcg cct atc tcg agc acg gac aag cag atc tcc ccg aac gcc         496
Gly Asp Ala Pro Ile Ser Ser Thr Asp Lys Gln Ile Ser Pro Asn Ala
            125                 130                 135 gag tcc gga acg gcg tac tcg aag ccg cgc cgg ctg cgg acc gac gag         544
Glu Ser Gly Thr Ala Tyr Ser Lys Pro Arg Arg Leu Arg Thr Asp Glu
        140                 145                 150 gtc ccc ggg atc gtc gac gac ttc agg cgg gcc gca cgg aac gcg gtc         592
Val Pro Gly Ile Val Asp Asp Phe Arg Arg Ala Ala Arg Asn Ala Val
    155                 160                 165 gag gct ggt ttc gac gcc gtc gag atc cac ggc gcg cac ggg tac ctc         640
Glu Ala Gly Phe Asp Ala Val Glu Ile His Gly Ala His Gly Tyr Leu
170                 175                 180                 185 ctg gag cag ttc atg aag gac agc tgc aac gac cgc acg gac cag tac         688
Leu Glu Gln Phe Met Lys Asp Ser Cys Asn Asp Arg Thr Asp Gln Tyr
                190                 195                 200 ggc ggc agc ctg gag aac cgg tgc cgt ctc gcc gtg gag gtc gtg gac         736
Gly Gly Ser Leu Glu Asn Arg Cys Arg Leu Ala Val Glu Val Val Asp
            205                 210                 215 gcc gtc gtc cgc gag gtg ggc gcg cgc cgc gtc ggc atc agg ctg tcg         784
Ala Val Val Arg Glu Val Gly Ala Arg Arg Val Gly Ile Arg Leu Ser
        220                 225                 230
```

| | | |
|---|---|---|
| ccc ttc gtc gac ttc gtg gac tgc gtg gac tcg gac ccg gtg gcg ctc<br>Pro Phe Val Asp Phe Val Asp Cys Val Asp Ser Asp Pro Val Ala Leu<br>235                        240                                  245 | 832 |
| ggc cac tac atg gtg cag cag ctc aac agg cat agc ggc ttg ctc tac<br>Gly His Tyr Met Val Gln Gln Leu Asn Arg His Ser Gly Leu Leu Tyr<br>250                        255                           260                   265 | 880 |
| tgc cac atg gtg gag ccc cgc att acc gcc cac ggg cgc agg cag atc<br>Cys His Met Val Glu Pro Arg Ile Thr Ala His Gly Arg Arg Gln Ile<br>                        270                           275                           280 | 928 |
| cct cac ggg ctc ttg ccg ttc cga aag gcg ttt cat gga acg ttc atc<br>Pro His Gly Leu Leu Pro Phe Arg Lys Ala Phe His Gly Thr Phe Ile<br>                  285                           290                           295 | 976 |
| gcc gcc ggt ggc ggt ggt tac gat cgg gag gaa ggc aac aag gtg gtg<br>Ala Ala Gly Gly Gly Gly Tyr Asp Arg Glu Glu Gly Asn Lys Val Val<br>300                        305                           310 | 1024 |
| gca gaa ggg tat gct gac ctc gtc gcg tat ggg aag ctg ttc ttg gct<br>Ala Glu Gly Tyr Ala Asp Leu Val Ala Tyr Gly Lys Leu Phe Leu Ala<br>        315                        320                           325 | 1072 |
| aac ccg gac ctg cct agg agg ttc gag ctg gat gtg gca ctc aac aaa<br>Asn Pro Asp Leu Pro Arg Arg Phe Glu Leu Asp Val Ala Leu Asn Lys<br>330                        335                           340                   345 | 1120 |
| tac gac cgc tcc acc ttc tac acg caa gat cct att gtt ggc tac aca<br>Tyr Asp Arg Ser Thr Phe Tyr Thr Gln Asp Pro Ile Val Gly Tyr Thr<br>                  350                           355                           360 | 1168 |
| gat tac cct ttc ttt gaa caa gaa gat ggc aag aat gag gag<br>Asp Tyr Pro Phe Phe Glu Gln Glu Asp Gly Lys Asn Glu Glu<br>                 365                           370                           375 | 1210 |
| tgaatctgat aatgtggagg gttcatcaag tataagttca tcattatttc caccattcat | 1270 |
| tattggccat tgtggtggag tcattgtgtc atgttgtttc attctgtact agtgtggtgt | 1330 |
| gaagtgaaat aaatctattt ggtgaaattg ttataaaata aattatagac ttgtcggatt | 1390 |
| taaaaaaaaa aaaaaaaa | 1409 |

<210> SEQ ID NO 4
<211> LENGTH: 375
<212> TYPE: PRT
<213> ORGANISM: Zea mays

<400> SEQUENCE: 4

Met Val Gln Gln Ala Ala Lys Glu Val Ile Pro Leu Leu Thr Pro Tyr
1               5                   10                  15

Lys Met Gly Gln Phe Glu Leu Ser His Arg Val Val Leu Ala Pro Leu
            20                  25                  30

Thr Arg Cys Arg Ser Tyr Gly Asn Val Pro Gln Pro His Ala Ala Val
        35                  40                  45

Tyr Tyr Ser Gln Arg Ala Thr Arg Gly Gly Leu Leu Ile Ala Glu Ala
    50                  55                  60

Thr Gly Val Ser Ala Thr Ala Gln Gly Phe Pro Glu Ser Pro Gly Ile
65                  70                  75                  80

Trp Thr Gln Glu Gln Val Glu Ala Trp Lys Pro Ile Val Asp Ala Val
                85                  90                  95

His Arg Lys Gly Ala Ile Phe Val Cys Gln Ile Trp His Val Gly Arg
            100                 105                 110

Val Ser Thr Asn Glu Leu Gln Pro Asn Gly Asp Ala Pro Ile Ser Ser
        115                 120                 125

Thr Asp Lys Gln Ile Ser Pro Asn Ala Glu Ser Gly Thr Ala Tyr Ser
    130                 135                 140

Lys Pro Arg Arg Leu Arg Thr Asp Glu Val Pro Gly Ile Val Asp Asp
145                 150                 155                 160

Phe Arg Arg Ala Ala Arg Asn Ala Val Glu Ala Gly Phe Asp Ala Val
                165                 170                 175

Glu Ile His Gly Ala His Gly Tyr Leu Leu Glu Gln Phe Met Lys Asp
            180                 185                 190

Ser Cys Asn Asp Arg Thr Asp Gln Tyr Gly Gly Ser Leu Glu Asn Arg
        195                 200                 205

Cys Arg Leu Ala Val Glu Val Asp Ala Val Val Arg Glu Val Gly
    210                 215                 220

Ala Arg Arg Val Gly Ile Arg Leu Ser Pro Phe Val Asp Phe Val Asp
225                 230                 235                 240

Cys Val Asp Ser Asp Pro Val Ala Leu Gly His Tyr Met Val Gln Gln
                245                 250                 255

Leu Asn Arg His Ser Gly Leu Leu Tyr Cys His Met Val Glu Pro Arg
            260                 265                 270

Ile Thr Ala His Gly Arg Arg Gln Ile Pro His Gly Leu Leu Pro Phe
        275                 280                 285

Arg Lys Ala Phe His Gly Thr Phe Ile Ala Ala Gly Gly Gly Tyr
    290                 295                 300

Asp Arg Glu Glu Gly Asn Lys Val Val Ala Glu Gly Tyr Ala Asp Leu
305                 310                 315                 320

Val Ala Tyr Gly Lys Leu Phe Leu Ala Asn Pro Asp Leu Pro Arg Arg
                325                 330                 335

Phe Glu Leu Asp Val Ala Leu Asn Lys Tyr Asp Arg Ser Thr Phe Tyr
            340                 345                 350

Thr Gln Asp Pro Ile Val Gly Tyr Thr Asp Tyr Pro Phe Phe Glu Gln
        355                 360                 365

Glu Asp Gly Lys Asn Glu Glu
370                 375

<210> SEQ ID NO 5
<211> LENGTH: 458
<212> TYPE: DNA
<213> ORGANISM: Zea mays

<400> SEQUENCE: 5
aaaagcttaa tcaaacgcgc cactagacaa gtgctcggat gcatgtacga gtacattgtg      60
aacgtagtag aatatcagtg cgtggacgag cacagaaatg tacacaggga tgatcagcga     120
agaagatcct acatgtaaaa tgccatattg cgtcatcact tagtgcaggt gacgttcact     180
tttcgcagca caagtcaaag aggcagcaat ctgtgaactt tgacgtgcgg cggttggagg     240
gttgcagccg acacacggcc tgttccaatg aacctgcgtg agcgccaagt ggatgacgga     300
aagggtgacg caacacccct ggagcgccca ctccgacaac tataaataca cagcgacacc     360
cttcttccag tagacgcaga acaagcagag cgagaaaccg agcaaagcta gtaagagcag     420
agagctgcaa gtgacctgcg gtgttgcatc acatctga                            458

<210> SEQ ID NO 6
<211> LENGTH: 770
<212> TYPE: DNA
<213> ORGANISM: Zea mays
<220> FEATURE:
<223> OTHER INFORMATION: n  at positions 3, 6, 9, 19, 425, 434, 572, 593,
      628, 637, 700, 704, 706, 728, and 747 can be a, t,
      g, or c

```
<400> SEQUENCE: 6
aancgnctna gaccacttng taatacgcct actataggga aagctggtac gcctgcaggt    60
accggtccgg aattcccggg ctcccttctc ccctccccgt tccctctccc aactccaatc   120
catggcctcc acggatcgct ccgcgccggc ggaggaccag caacagccgc agcgcccgtc   180
cctcttctcg ccgtaccaga tgccccactt ccgcctcgcg caccgggtgg tgctggcgcc   240
gatgaccagg tgccgggcgc ccgatgcgct cccgggcccc gcgctcgcgg agtactacgc   300
gcagcggtcc acgaaggcg gcttgctcat tcccgagggc accatcatct cgcccgtcgg   360
acctgggttc ctcgtgtccc tgggatatac aatcaagagc agactgatgc atggaaaaag   420
gtggntgatg ctgntcatgc aagggagcc atctttttct gcaactatgg catgtaggtc    480
gagcttttac caagtatatc agccgggtgg tctgctccaa tatcctctac tgataaacca   540
atatcatcaa gatggaggat actgatgccc gntggatcct atggcaagga atncaacttc   600
caggcgctag ccacattcga gataccanaa attgtcnagc aatacccgac agggcttggc   660
ataaacgcca tcaaagcaag gtttcgatgg gatcgagatn cacngnggcc catgggtacc   720
taatcganca gttctaagga cggtatnaac gacagggtta ccaattacgg              770

<210> SEQ ID NO 7
<211> LENGTH: 641
<212> TYPE: DNA
<213> ORGANISM: Zea mays
<220> FEATURE:
<223> OTHER INFORMATION: n  at positions 24, 44, 71, 81, 98, 332, 358,
      389, 406, 433, 451, 475, 497, 531, 535, 560, 590, 592,
      602, and 619  can be a, t, g, or  c

<400> SEQUENCE: 7
gcccaactac ccgctccctg tggngcgtcc agcgtgcaac caanacctcc cacgagtccg    60
cgacgcgtca ncgtggaccg nccgtcgtcg caaacgancc cagtggcgat tcgctttcga   120
accgcactcg ccctcctccg ttctcttctc tccctcctcc tatagttggc ttctcgcaac   180
cctctgcttt cgatcagctt tctccgctcc ccatttccct ctccaactcc aatccatggc   240
ctccacggat cgctccacgc cggcggagga cgagcaacag cagaagcgcc cgtctctctt   300
ctcgccgtac cagatgcccc gcttccgcct cncccaccgg gtggtgctgg cgccgatnac   360
caggtgcagg gcgcccgacg cggtcccang ccccgcgctc gcggantact acgcgcagcg   420
gtccacggac ggnggcttgc tcatctccga nggcaccatc atctcgccgt ccggncctgg   480
gttccctcgt gttcctngga tatacaatca aaaaaaaat gatgcatgga naangtggt    540 tgatgctgtt catgcccaan ggaactatct ttttcttgcc aactatggan tntttgccaa   600
cntctcccca atttatcanc cggtctgctg tccattccca a                      641

<210> SEQ ID NO 8
<211> LENGTH: 496
<212> TYPE: DNA
<213> ORGANISM: Zea mays
<220> FEATURE:
<223> OTHER INFORMATION: n  at positions 5, 29, 30, 43, 49, 109, and 189
      can be a, t, g, or  c

<400> SEQUENCE: 8
ctaanacgac tcactaaagg gaaaaacann aacgcctgca ggnaccggnc cggaattccc    60
gggtcgaccc acgcgtccgc ccacgcgtcc gcccacgcgt ccgcccacnc gtccggcaaa   120
gcgcagagct agcaagtgac cgaccgagag caaataggca aggcaacgca ggcaagatgg   180
```

```
                                    -continued tgcagcaanc cgcgaaggag gtgatccgc tgctgacgcc ttacaagatg gggcagttcg      240
agctctctca ccgggtggtg ctggcgccgc tgacgaggtg ccgctcctac ggcaacgtgc      300
cgcagccaca cgccgccgtg tactactcgc agcgcgccac cagggtggc ctgctcatcg      360 cggaggccac gggggtgtcg gccaccgcgc aggggttccc ggagtctcct ggcatctgga      420
cgcaggagca ggtcgaggcg tggaagccca tcgtcgacgc cgtccaccgc aaggcgccat      480
cttcgtctgc cagatt                                                      496

<210> SEQ ID NO 9
<211> LENGTH: 555
<212> TYPE: DNA
<213> ORGANISM: Zea mays

<400> SEQUENCE: 9
catctgttta gccaagctgt ggccaacctc tgacgaggaa tggagatgga gtcgactcct       60
ctcttgacac catacaagat gggcgatttc aacctggcac acaggttgt gctggcgccg      120 ctgacgaggt gccgggcgtt cgggaacgtg ccgcagccgg agcacatggc tctctactac      180
cgccagcggg cgacgcccgc gggcttcctc atcgccgagg cctgcgccgt gtcggagagc      240
gcgcgcgggt acccggacgt tccgggggct gtggacccac caacaggtcg aggcctggaa      300
gccgatcgtc gacgccgtcc acgccagcgg tgccgtcttc ttcgcccagc tctggcacac      360
cggccgggcc tccccctcag aattccaacc aaatgggcag gcaccgatct ctagcacgga      420
caagcaaatc ccagcacagg tgaaccattc cggtgactca acacgttcgc ggtgctcgga      480
gatagagaca gaggagatac cacacgtcgt caatgaattc cgggttgccg gccaaaaaaa      540
ggccatcaaa gcagg                                                       555
```

POLYNUCLEOTIDES ENCODING MONOCOT 12-OXO-PHYTODIENOATE REDUCTASES AND METHODS OF USE

CROSS-REFERENCE TO RELATED APPLICATIONS

This application claims the benefit of U.S. Provisional Application Nos. 60/134,808 and 60/134,911, both filed on May 19, 1999.

FIELD OF THE INVENTION

The present invention relates to the field of plant molecular biology, particularly to the isolation of genes and their promoters. The invention further relates to the use of the genes and promoters to modify biochemical processes in plants.

BACKGROUND OF THE INVENTION

Throughout their lives, plants are routinely subjected to a variety of stresses, which act to impede or alter growth and development processes. Stresses to plants may be caused by both biotic and abiotic agents. For example, biotic causes of stress include infection with a pathogen, insect feeding, and parasitism by another plant such as mistletoe, and even grazing by ruminant animals. Abiotic stresses include osmotic stress, excessive light intensity or insufficient light intensity, cold temperatures, warm temperatures, synthetic chemicals such as those used in agriculture, and excessive wind.

Because a stress negatively impacts plant growth and development processes, stress to agricultural plants has a negative economic impact expressed in the form of reduced yields, increased expenditures for pesticides or both. Developing crop plants that are better able to tolerate or even avoid stresses is desirable and will most certainly improve agricultural productivity. Given the world's increasing human population and diminishing land area available for agriculture, improving agricultural productivity is a paramount challenge. A thorough understanding of the mechanisms used by plants to avoid or to tolerate stresses may help in the development of new strategies of improving the stress tolerance of agricultural plants.

In spite of the great frequency of stresses, plants survive, and often flourish. Plants are able to do this because of the evolution of a variety of internal and external mechanisms for avoiding or tolerating stress. For example, higher plants possess leaves with waxy, water-impermeable surfaces and pores known as stomata, which serve to allow the escape of water vapor during the process of transpiration. The periphery of the stomatal pores is lined with a pair of cells known as guard cells, which control the aperture of the pore. By modifying their size and shape through a turgor-pressure-mediated process, the guard cells can completely block the pore when conditions are unfavorable for transpiration during, for example, periods of low soil-water availability. Such a stress-avoidance system allows a plant to survive conditions of water stress by reducing transpiration to nearly zero and preventing dehydration.

Plants also possess defense systems for helping to limit the stresses resulting from attacks by pathogens and insects. One well-known defense system against plant pathogens is known as systemic acquired resistance. Another defense system is the systemic induction of proteinase inhibitors following insect damage, which is usually referred to as the systemic wound response. In both of these defense systems, the initial impact of the pathogen or insect is transmitted via a signal or signals to other parts of the plant which results in increased expression of genes encoding proteins that are directly or indirectly inhibitory to invading organisms. The associated, systemic increase in defense gene products is known to increase the resistance of the plant to both current and future stresses from pathogens and insects.

Despite the general similarities of the two systems, most of the components, such as signal molecules and defense genes, are distinct for the two defense systems. In systemic acquired resistance, salicylic acid is an important signal molecule, which acts to promote the resistance response in the plant. However, salicylic acid does not promote the systemic wound response, and in fact, there is some evidence to suggest that salicylic acid may act to repress the systemic wound response (Pena-Cortes et al. (1993) *Planta* 191:123–128; Doherty and Bowles (1990) *Plant Cell Environ* 13:851–858. Similarly, jasmonates are known to serve as signal molecules that promote the systemic wound response, but do not serve in a similar capacity in systemic acquired resistance.

The jasmonates are a group of naturally occurring molecules derived from the oxygenation of tri-unsaturated fatty acids and are distinguished by the presence of a cyclopentanone ring. Plants produce two of the most well-known members of the jasmonate family, jasmonic acid and its methyl ester, the perfume oil, methyl jasmonate. In plants, these compounds are synthesized from linolenic acid through a branch of a larger biochemical pathway known as the lipoxygenase pathway. This pathway was named for its first enzyme, lipoxygenase, which catalyzes the formation of lipid hydroperoxides from certain unsaturated fatty acids, which possess two or more double bonds. Because the predominant lipoxygenase substrates in plants are the eighteen-carbon fatty acids, linoleic acid and linolenic acid, the lipoxygenase pathway has been occasionally referred to as the octadecanoid pathway.

More recently, however, the lipoxygenase pathway has been referred to as the oxylipin pathway. Oxylipins, as their name implies, are oxygenated lipid molecules, which result from the oxygenation of unsaturated fatty acids via the lipoxygenase reaction and also include any molecules, irrespective of oxygenation status, derived from such oxygenated lipids. Given that jasmonates originate from the lipoxygenase-catalyzed synthesis of lipid hydroperoxides, they are oxylipins.

New strategies are needed for improving agricultural plants. While traditional plant breeding approaches will continue to be important for improving agricultural plants, the new strategies that are likely to have the most significant impact on crop improvement will involve genetic engineering.

SUMMARY OF THE INVENTION

Methods and compositions for expressing genes encoding homologues of Old Yellow Enzyme (OYE) are provided. The compositions comprise nucleotide sequences encoding monocot homologues of OYE, particularly those with a 12-oxo-phytodienoate reductase activity. The compositions further comprise antisense sequences of such nucleotide sequences. The sequences are useful in transforming plants for constitutive and stress-induced expression of sense and antisense sequences for homologues of OYE. Such compositions find use in methods for increasing stress resistance, modifying growth and altering oxylipin metabolism in plants.

Also provided are methods and compositions for regulating the expression of a nucleotide sequence in a plant in response to a stimulus. The compositions comprise promoters from genes encoding OYE homologues. Such promoters are useful in transforming plants for increasing the expression of a nucleotide sequence in response to a stimulus such as infection with a pathogen, insect or nematode feeding, and application of jasmonic acid and osmotic stress. Such sequences find use in increasing the resistance of plants to pests and pathogens and as well abiotic stresses.

Expression cassettes comprising sequences of the invention are provided. Additionally provided are transformed plants, plant tissues, plant cells and seeds thereof. Isolated proteins encoded by the sequences of the invention are provided.

BRIEF DESCRIPTION OF THE DRAWINGS

FIG. 1 depicts the results of a Northern blotting experiment to determine changes on ZmOYE transcript levels. Isolated RNA was subjected to Northern blot analysis using a radiolabeled ZmOYE1 probe.

FIG. 2 depicts the results of a Northern blotting experiment to determine the effect of inoculating maize suspension cultures with spores of *Fusarium moniliforme* on the level of ZmOYE transcripts. As an RNA loading control, a Northern blot to detect actin transcripts was also conducted.

DETAILED DESCRIPTION OF THE INVENTION

Figure 1A:
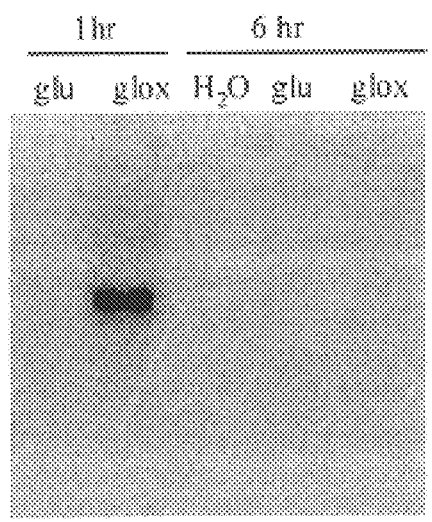
FIG. 1A depicts the effect of an oxidative burst caused by the addition of glucose and glucose oxidase on the expression of ZmOYE transcripts in a maize suspension cultures. Total RNA was isolated from maize suspension cells treated with $H_2O$, 6 mM glucose (glu), or 6 mM glucose with 25 mg/ml glucose oxidase (glox) for time periods indicated in the figure. An oxidative burst was generated by the addition of glucose and glucose oxidase.

A number of terms used herein are defined and clarified in the following section.

By "biotic stress" is intended any stress to a plant that is caused by presence or activities of a non-human organism including, but not limited to, animals, plants, fungi, bacteria and viruses.

By "abiotic stress" is intended any stress to a plant that is not caused by the presence or activities of a non-human organism. Such an abiotic stress include, for example, high temperatures, low temperatures, drought, flooding, excessive light intensity, insufficient light intensity, high salinity conditions, insufficient available nutrients, air pollution, acid rain, heavy metals, synthetic chemicals, naturally occurring chemicals applied to the environment by humans and stresses caused by agricultural practices including stresses resulting from the application of pesticides, herbicides and fertilizers.

By "pathogen" is intended any organism that has the potential to negatively impact a plant, typically, but not exclusively, by causing disease or inflicting damage physical. Such organisms include, but are not limited to, fungi, bacteria, nematodes, insects and viruses.

By "insect" is intended any animal that is taxonomically classified as an insect as well as similar herbivores such as acarids.

By "agronomic trait" is intended a phenotypic trait of an agricultural plant that contributes to the performance or economic value of the plant. Such traits include disease resistance, insect resistance, nematode resistance, virus resistance, drought tolerance, high salinity tolerance, yield, plant height, days to maturity, seed nitrogen content, seed oil content, seed or fruit color, seed or fruit size and the like.

By "developmental process" is intended any process which contributes to the growth and development of a plant. Examples of such processes include fruit ripening, organ growth, cell division, cell elongation, senescence, germination, respiration, photosynthesis, transpiration, flowering, pollination and fertilization.

By "nucleotide molecule" is intended a molecule composed of nucleotides covalently bound to one another. Nucleotides include both ribonucleotides and deoxyribonucleotides. "Nucleotide molecule" encompasses single-stranded and double stranded forms of both DNA and RNA. "Nucleotide molecules" may be naturally occurring, synthetic or a combination of both. The linear arrangement of nucleotides in a "nucleotide molecule" is referred to as a "nucleotide sequence" and unless specified otherwise is presented herein from left to right corresponding to 5'-to-3' direction.

By "variants" is intended substantially similar sequences. For nucleotide sequences, conservative variants include those sequences that, because of the degeneracy of the genetic code, encode the amino acid sequence of one of the encode the amino acid sequence of the 12-oxo-phytodienoate reductase or the OYE homologue polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a 12-oxo-phytodienoate reductase or OYE homologue protein of the invention. Generally, variants of a particular nucleotide sequence of the invention will have at least 40%, 50%, 60%, 70%, generally at least 75%, 80%, 85%, preferably about 90% to 95% or more, and more preferably about 98% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, 12-oxo-phytodienoate reductase activity as described herein. Such variants may result from, for example, genetic polymorphism or from human manipulation. Biologically active variants of a 12-oxo-phytodienoate reductase or a OYE homologue protein of the invention will have at least 40%, 50%, 60%, 70%, generally at least 75%, 80%, 85%, preferably about 90% to 95% or more, and more preferably about 98% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

By "antisense nucleotide sequence" is intended a sequence that is in inverse orientation to the normal 5'-to-3' orientation of that nucleotide sequence. When delivered into a plant cell, the antisense DNA sequence prevents normal expression of the nucleotide sequence for the native gene. An antisense nucleotide sequence is said to "correspond to" a particular nucleotide sequence when the antisense nucleotide sequence is complementary to and capable of hybridizing to that particular nucleotide sequence. The antisense nucleotide sequence encodes an RNA transcript that is complementary to and capable of hybridizing to the endogenous messenger RNA (MRNA) produced by transcription of the DNA sequence for the native gene. Expression of the antisense transcript RNA interferes with expression of the corresponding MRNA and hence disrupts production of the native protein.

By "OYE homologue" is intended a protein that is member of the Old Yellow Enzyme (OYE) family. Generally, members of this family display an amino acid similarity of greater than 35%, preferably greater than 45%, when their amino acid sequences are aligned and compared with the amino acid sequences of yeast OYEs such as OYE1 (GenBank Accession No. Q02899), OYE2 (GenBank Accession No. Q03558) and OYE3 (GenBank Accession No. P41816) using a standard sequence alignment algorithm. For the present invention, the preferred method for determining amino acid sequence similarities is BESTFIT (Wisconsin Genetics Software Package, Version 10.0, Genetics Computer Group, Madison, Wis.) using the default parameters. In addition, amino acids that comprise both the FMN-binding site and the catalytic site are generally conserved in "OYE homologues." See, Schaller and Weiler (1997) *J. Biol. Chem.* 272:28066–28072 for a description of amino acid residues that contribute to the FMN-binding and catalytic sites of OYE homologues.

Methods for modifying oxylipin metabolism in plants are provided. The methods find use in modifying developmental processes in plants and in increasing the resistance of plants to biotic and abiotic stresses. Such methods also find use in producing specific oxylipins in plants such as the perfume, methyl jasmonate. The methods comprise stably incorporating in the genome of a plant a nucleotide sequence comprising a coding sequence for a 12-oxo-phytodienoate reductase, particularly from a plant, more particularly from a monocot, most particularly from maize. Preferably, such sequences encode 12-oxo-phytodienoate reductases that are homologues of Warburg's Old Yellow Enzyme (OYE). However, it is recognized that all 12-oxo-phytodienoate reductases may not be homologues of OYE. Thus, the invention encompasses all 12-oxo-phytodienoate reductases, not only those that are OYE homologues. Because OYE itself is a 12-oxo-phydienoate reductase (Schaller and Weiler (1997) *J. Biol. Chem.* 272:28066–28072), nucleotide sequences encoding OYE may also be used in the methods of invention.

The coding sequences of the invention are operably linked to promoters that drive expression of the sequence in a plant cell. Any one of a variety of promoters, including the native promoters, can be used with the sequences of the invention depending on the desired timing and location of expression. Preferred promoters include constitutive, pathogen-inducible, insect-inducible, nematode-inducible, wound-inducible, tissue-preferred, developmentally regulated and chemically regulatable promoters. The invention encompasses plant cells, plant tissues, plants and seeds thereof.

The sequences of the invention can be used to modulate the oxylipin biosynthetic pathway. By "modulate" is intended increasing or decreasing overall carbon flux through the pathway, increasing or decreasing the level of any specific precursor, intermediate or product of the pathway or combinations thereof. The oxylipin pathway produces molecules such as anti-pathogenic, volatiles cis-3-hexenol and trans-2-hexenal, and the jasmonates which are involved in defense mechanisms, osmotic regulation, fruit ripening, production of viable pollen, root growth, tendril coiling, and senescence. Thus, modulation of the oxylipin pathway may modulate these physiological processes.

In particular, a 12-oxo-phytodienoate reductase can be used to control the flow metabolites from the 18-carbon group to the 12-carbon group of cyclic α-linolenic acid derivatives. The expression of this enzyme can prime or up-regulate the octadecanoid pathway.

In addition to 12-oxo-phytodienoate reductase nucleotide sequences, nucleotide sequences comprising coding sequences of other enzymes involved in oxylipin metabolism may be utilized to shunt biosynthesis into particular metabolites of interest. The use of such sequences may be necessary to enhance the production of specific oxylipins including, for example, jasmonic acid and methyl jasmonate. Examples of such coding sequences include, but are not limited to, sequences encoding a phospholipase $A_2$ (May et al. (1998). *Biochim. Biophys. Acta* 1393:267–276), a lipoxygenase (Bell and Mullet (1993) *Plant Physiol.* 103:1133–1137; Saravitz and Siedow. (1996) *Plant Physiol.* 110:287–299), an allene oxide synthase (Laudert et al. (1996) *Plant Mol. Biol.* 31:323–335), an allene oxide cyclase (Hamberg and Fahlstadius (1990) *Arch. Biochem. Biophys.* 276:518–526), a hydroperoxide lyase (Bate et al. (1998) *Plant Physiol.* 117:1393–1400), an enzyme involved in β-oxidation such as acyl-CoA oxidase (GenBank Accession Nos. AF057043 and AF057044) or combinations thereof may used. These sequences in either sense or anti-sense orientations can be operably linked to promoters such as those described supra, and the resulting DNA constructs can be used to genetically manipulate a plant to express the desired nucleotide sequence or sequences in addition to 12-oxo-phytodienoate reductase sequences.

In a preferred method for modifying oxylipin synthesis in plant, an antisense sequence encoding a 12-oxo-phytodienoate reductase is utilized to lower or eliminate the expression of at least one native 12-oxo-phytodienoate reductase gene in a plant. It is recognized that decreasing or eliminating 12-oxo-phytodienoate reductase activity in a plant can lead to the accumulation of 12-oxo-phytodienoic acid and other upstream intermediates in the oxylipin pathway. By decreasing or eliminating 12-oxo-phytodienoate reductase activity, the plant can shunt oxylipin metabolism toward hydroperoxide lyase, resulting in the increased synthesis of the anti-pathogenic volatiles, cis-3-hexenol and trans-2-hexenal.

The role of jasmonates as signal molecules in systemic wound responses is well established. Until recently, the jasmonates were not known to be involved in plant defense responses against pathogens. Results from recent investigations with both rice and Arabidopsis thaliana plants have revealed that jasmonates may play a role in plant defenses against pathogens (Schweizer et al. (1998) Plant J. 14:475–481; Vijayan et al. (1998) Proc. Natl. Acad. Sci. 95:7209–7214; Staswick et al. (1998) Plant J. 15:747–754). In addition to their roles in plant defense responses to pathogens and insects, jasmonates have been implicated in responses to osmotic stresses such as drought and high salt conditions as well as in the mediation of variety of growth and developmental processes in plants (Wasternack and Parthier (1997) Trends in Plant Science 2:302–307).

Methods for increasing the resistance of a plant to biotic and abiotic stress and for altering plant growth and development processes are additionally provided. Such methods find use in improving agronomic traits of agricultural plants. The methods comprise modifying oxylipin metabolism as described supra. In each of the methods, the level of at least one oxylipin in a plant will be altered. It is recognized that controlling the timing and location of such an alteration in the level of an oxylipin will be essential to achieving the desired outcome. It is further recognized that the choice of promoter used to control the expression of 12-oxo-phytodienoate reductase sequences and any other gene or genes involved in oxylipin metabolism that are utilized in these methods, will be critical to controlling the timing and location of such an alteration in the level of an oxylipin.

An embodiment of the methods for increasing the resistance a plant to a stress, particularly biotic stress resulting from infection by a pathogen, comprises stably transforming plants with nucleotide sequences encoding Old Yellow Enzyme homologues that catalyze in plants the formation of reactive oxygen species or promote their formation indirectly by catalyzing the formation of an intermediate in a pathway that leads to the formation of reactive oxygen species. It is recognized that such routes to reactive oxygen species may depend on the NADH oxidase activity that is associated with Old Yellow Enzyme homologues. While the invention is not dependent on any particular mechanism, increasing the formation of reactive oxygen species may be essential to increasing the resistance of plants to certain stresses.

Methods for producing specific oxylipins in plants are provided. The methods find use in the production of valuable chemicals such as the perfume methyl jasmonate and jasmonic acid. Further it is recognized that the methods of the invention produce biologically active stereoisomers of oxylipins. For example, there are four possible stereoisomers of both methyl jasmonate and jasmonic acid. Commercially produced, synthetic methyl jasmonate is composed of all four stereoisomers (Creelman et al. (1997) Ann. Rev. Plant Physiol. Plant Mol. Biol. 48:355–381). However, the biosynthesis of both methyl jasmonate and jasmonic acid in planta yields only a single stereoisomer, respectively (Creelman et al. (1997) Ann. Rev. Plant Physiol. Plant Mol. Biol. 48:355–381). The methods of the invention produce only the biologically active stereoisomers of oxylipins that occur naturally in plants. The methods comprise modifying oxylipin metabolism in a plant by stably incorporating nucleotide sequences encoding enzymes involved in oxylipin metabolism operably linked to promoters that drive expression in a plant. Such enzymes include, but are not limited to, a 12-oxo-phytodienoate reductase encoded by the sequences of the invention, a phospholipase $A_2$ (May et al. (1998). Biochim. Biophys. Acta 1393:267–276), a lipoxygenase (Bell et al. (1993) Plant Physiol. 103:1133–1137; Saravitz and Siedow (1996) Plant Physiol. 110:287–299), an allene oxide synthase (Laudert et al. (1996) Plant Mol. Biol. 31:323–335), an allene oxide cyclase (Hamberg et al. (1990) Arch. Biochem. Biophys. 276:518–526), a hydroperoxide lyase (Bate et al. (1998) Plant Physiol. 117:1393–1400) and an enzyme involved in β-oxidation such as acyl-CoA oxidase (GenBank Accession Nos. AF057043 and AF057044). Such enzymes can be used alone or in combination and if desired, directed to a particular cellular compartment by operably linking a nucleotide sequence that encodes a targeting signal for a specific compartment to the nucleotide sequence encoding the enzyme. Preferred compartments for localizing such enzymes include the chloroplast, peroxisomes and cytoplasm.

Compositions of the invention include the native nucleotide sequences for 12-oxo-phytodienoate reductase genes, homologues of OYE, antisense sequences, as well as variants and fragments thereof. Particularly, the genes encoding the OYE homologues of maize and their respective amino acid sequences for the proteins encoded thereby, as well as fragments and variants thereof are provided. These nucleotide and amino acid sequences are set forth in FIGS. 1 to 4 (SEQ ID NOs: 1–4). The nucleotide sequences or corresponding antisense sequences find use in modulating the expression of a 12-oxo-phytodienoate reductase or an OYE homologue in a plant or plant cell. That is, the coding sequences are used to increase the expression while antisense sequences are used to decrease expression. Expression cassettes comprising a nucleotide sequence of the invention operably linked to a promoter that drives expression in a plant cell are provided.

Promoter sequences for the genes of the invention are also provided (SEQ ID NO: 5). The promoters find use in methods for regulating transcription of a gene in response to a stimulus such as, for example, an infection with a pathogen, damage from insect feeding, drought, ozone and high and low temperatures. The methods comprise stably incorporating into the genome of a plant a DNA construct comprising a promoter which comprises a nucleotide sequence from a monocot 12-oxo-phytodienoate reductase gene or from a gene encoding a monocot homologue of OYE operably linked to a second nucleotide sequence. Such second nucleotide sequences include, but are not limited to, coding sequences. The coding sequences can be from the same gene as the promoter of the invention or can be heterologous coding sequences. By "heterologous coding sequence" is intended any coding sequence that is not the native coding sequence from the same gene as the promoter of the invention. Such heterologous coding sequences include, but are not limited to, naturally occurring sequences, modified or optimized coding sequences and other synthetic sequences.

Although the promoters of the invention can be operably linked to any one of a variety of second nucleotide sequences, preferred embodiments of the invention encompass those second nucleotide sequences that, when expressed in a plant, help the plant to alleviate, tolerate or recover from a stressful stimulus such as, for example, one of the stimuli described supra. It is recognized that such nucleotide sequences may be used in either the sense or antisense orientation depending on the desired outcome. Examples of such nucleotide sequences include, but are not limited to, sequences encoding glutathione S-transferase (GenBank Accession Nos. X79515, X04375, U14599, U12679 and M16901), glutathione peroxidase (GenBank Accession Nos. X89866, AJ000470, AJ000469, AA753209 and U94495), a bifunctional protein with both glutathione S-transferase activity and glutathione peroxidase activity (GenBank Accession Nos. X68304 and X56266), ferritin (GenBank Accession Nos. X61392 and X61391), catalase (GenBank Accession Nos. X54819, X12538 and M33103) and superoxide dismutase (GenBank Accession Nos. X17564, X17565, M33119 and M15175).

Methods for increasing the resistance of plant to a stress utilizing the promoters of the invention operably linked to a second nucleotide sequences are provided. The methods find use in agriculture for improving the resistance of crop plants to stresses. The preferred second nucleotide sequences are those described supra that, when expressed in a plant, help the plant to alleviate, tolerate or recover from a stressful stimulus such as, for example, one of the stimuli described supra. The methods of the invention involve transforming a plant with a promoter of the invention operably linked to the second nucleotide sequence.

Compositions of the invention include the native nucleotide sequences comprising the promoters of 12-oxo-phytodienoate reductase genes and OYE homologues, as well as naturally occurring and synthetic variants and fragments thereof. Particularly, the promoters of 12-oxo-phytodienoate reductase genes and OYE homologue genes of maize as well as fragments and variants thereof are provided. The nucleotide sequence of a maize ZmOYE promoter is set forth in SEQ ID NO: 5. Expression cassettes are provided comprising a promoter of the invention operably linked to a second nucleotide sequence which is expressed under the control of the promoter.

Plasmids containing the nucleotide sequences of the invention were deposited on Apr. 2, 1999 with American Type Culture Collection (ATCC), Manassas, Va., and assigned Accession No. 207188. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may or may not encode protein fragments that retain the biological activity of the native 12-oxo-phytodienoate reductase or OYE homologue. Alternatively, fragments of a nucleotide sequence of a promoter of the invention may or may not retain any promoter activity. Thus, fragments of a nucleotide sequence may range from at least about 20 nucleotides, about 50 nucleotides, about 100 nucleotides, and up to the entire promoter or nucleotide sequence encoding the 12-oxo-phytodienoate reductase or OYE homologue of the invention. Fragments of the invention include antisense sequences used to decrease expression of the 12-oxo-phytodienoate reductase genes and OYE homologue genes. Such antisense fragments may vary in length ranging from at least about 20 nucleotides, about 50 nucleotides, about 100 nucleotides, up to and including the full-length nucleotide sequence of the invention.

A fragment of a 12-oxo-phytodienoate reductase or OYE homologue nucleotide sequence that encodes a biologically active portion of a protein of the invention will encode at least 15, 25, 30, 50, 100, 150, 200, 250, 300 or 350 contiguous amino acids, or up to the total number of amino acids present in a full-length protein of the invention (for example, 375 amino acids for both SEQ ID NOs: 2 and 4). Fragments of a 12-oxo-phytodienoate reductase or OYE homologue nucleotide sequence that are useful as hybridization probes for PCR primers generally need not encode a biologically active portion of a 12-oxo-phytodienoate reductase or OYE homologue.

Thus, a fragment of an OYE homologue nucleotide sequence may retain some promoter activity, may encode a biologically active portion of an OYE homologue, or may be a fragment that can be used as a hybridization probe or PCR primer using methods disclosed below. A biologically active portion of an OYE homologue can be prepared by isolating a portion of one of the OYE homologue nucleotide sequences of the invention, expressing the encoded portion of the OYE homologue (e.g., by recombinant expression in vitro), and assessing the activity of the portion of the OYE homologue. Nucleic acid molecules that are fragments of an OYE homologue nucleotide sequence comprise at least 19, 20, 50, 75, 100, 150, 200, 250, 300, 350, 400, 450, 500, 550, 600, 650, 700, 800, 900, 1,000, 1,100, 1,200, 1,300, or 1,400 nucleotides, or up to the number of nucleotides present in a full-length OYE homologue nucleotide sequence or promoter sequence disclosed herein (for example, 1465, 1409, 458, 770, 641, 496, and 555 nucleotides for SEQ ID NOs: 1, 3, 5, 6, 7, 8 and 9, respectively).

It is recognized that with these nucleotide sequences, antisense constructions, complementary to at least a portion of the messenger RNA (mRNA) for the OYE homologue sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous OYE homologue genes in plants. Methods for suppressing gene expression in plants using nucleotide sequences in the sense orientation, also known as co-suppression methods, are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The use of the term "DNA constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the DNA constructs of the present invention encompass all nucleotide constructs which can be employed in the methods of the present invention for transforming plants including, but not limited to, those comprised of deoxyribonucleotides, ribonucleotides and combinations thereof. Such deoxyribonucleotides and ribonucleotides include both naturally occurring molecules and synthetic analogues. The DNA constructs of the invention also encompass all forms of nucleotide constructs including, but not limited to, single-stranded forms, double-stranded forms, hairpins, stem-and-loop structures and the like.

Furthermore, it is recognized that the methods of the invention may employ a DNA construct that is capable of directing, in a transformed plant, the expression of at least one protein, or at least one RNA, such as, for example, an rRNA, a tRNA and an antisense RNA that is complementary to at least a portion of an mRNA. Typically such a DNA construct is comprised of a coding sequence for a protein or an RNA operably linked to 5' and 3' transcriptional regulatory regions. Alternatively, it is also recognized that the methods of the invention may employ a DNA construct that is not capable of directing, in a transformed plant, the expression of a protein or RNA.

The DNA constructs of the invention also encompass nucleotide constructs, that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821 and Beetham et al. (1999) *Proc. Natl. Acad Sci. USA* 96:8774–8778; herein incorporated by reference.

The proteins of the invention may be altered in various ways including amino acid substitutions, deletions, truncations, and insertions. Methods for such manipulations are generally known in the art. For example, amino acid sequence variants of the OYE homologues can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired enzymatic activity, such as, for example, 12-oxo-phytodienoate reductase activity or NADH oxidase activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by enzyme activity assays. See, for example, Schaller and Weiler (1997) *J. Biol. Chem.* 272:28066–28072, herein incorporated by reference.

The nucleotide sequences encoding the 12-oxo-phytodienoate reductase or OYE homologues of interest can be the naturally occurring sequence cloned from a 12-oxo-phytodienoate reductase gene or OYE homologue gene, or they may be synthetically derived sequences.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire OYE homologue nucleotide sequences set forth herein or to fragments thereof are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2nd ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, oligonucleotides or degenerate oligonucleotides, and may be labeled with a detectable group such as $^{32}P$, or any other detectable marker. Thus, for example, probes for hybridization can be made by labeling synthetic oligonucleotides based on the OYE homologue sequences of the invention. Methods for preparation of probes for hybridization and for construction of cDNA and genomic libraries are generally known in the art and are disclosed in Sambrook et al. (1989) *Molecular Cloning: A Laboratory Manual* (2nd ed., Cold Spring Harbor Laboratory Press, Plainview, N.Y.).

For example, an entire OYE homologue sequence disclosed herein, or one or more portions thereof, may be used as a probe capable of specifically hybridizing to corresponding OYE homologue sequences and messenger RNAs. To achieve specific hybridization under a variety of conditions, such probes include sequences that are unique among OYE homologue sequences and are preferably at least about 10 nucleotides in length, and most preferably at least about 20 nucleotides in length. Such probes may be used to amplify corresponding OYE homologue sequences from a chosen organism by PCR. This technique may be used to isolate additional coding or promoter sequences from a desired organism or as a diagnostic assay to determine the presence of coding or promoter sequences in an organism. Hybridization techniques include hybridization screening of plated DNA libraries (either plaques or colonies; see, for example, Sambrook et al. (1989) *Molecular Cloning: A Laboratory Manual* (2nd ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.$+16.6$ (log M)$+0.41$ (%GC)$-0.61$ (% form)$-500/L$; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al, eds. (1995) *Current Protocols in Molecular Biology*, Chapter 2 (Greene Publishing and Wiley-Interscience, New York). See Sambrook et al. (1989) *Molecular Cloning: A Laboratory Manual* (2nd ed., Cold Spring Harbor Laboratory Press, Plainview, N.Y.).

In general, sequences that have promoter activity or encode for OYE homologue and hybridize to the OYE homologue sequences disclosed herein will be at least 40% to 50% homologous, about 60% to 70% homologous, and even about 80%, 85%, 90%, 95% to 98% homologous or more with the disclosed sequences. That is, the sequence identity of sequences may range, sharing at least about 40% to 50%, about 60% to 70%, and even about 80%, 85%, 90%, 95% to 98% sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller (1988) CABIOS 4:11–17;

the local homology algorithm of Smith et al. (1981) Adv. Appl. Math. 2:482; the homology alignment algorithm of Needleman and Wunsch (1970) J. Mol. Biol. 48:443–453; the search-for-similarity-method of Pearson and Lipman (1988) Proc. Natl. Acad. Sci. 85:2444–2448; the algorithm of Karlin and Altschul (1990) Proc. Natl. Acad. Sci. USA 872264, modified as in Karlin and Altschul (1993) Proc. Natl. Acad. Sci. USA 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237–244 (1988); Higgins et al. (1989) CABIOS 5:151–153; Corpet et al. (1988) Nucleic Acids Res. 16:10881–90; Huang et al. (1992) CABIOS 8:155–65; and Pearson et al. (1994) Meth. Mol. Biol. 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.hlm.nih.gov. Alignment may also be performed manually by inspection. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) J. Mol. Biol. 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) Proc. Natl. Acad. Sci. USA 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The nucleotide sequences of the invention are provided in expression cassettes for expression in the plant of interest. When an nucleotide sequence encoding an OYE homologue or 12-oxo-phytodienoate reductase is used, the cassette will include 5' and 3' regulatory sequences operably linked to an OYE coding sequence of the invention. When an OYE promoter sequence is used, the cassette will include the OYE promoter and 3' regulatory sequences operably linked to a second nucleotide sequence. Such an expression cassette may contain other 5' regulatory sequences in addition to the OYE promoter sequence. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be co-transformed into the organism. Alternatively, the additional gene(s) can be provided on multiple expression cassettes.

Such an expression cassette is provided with a plurality of restriction sites for insertion of the nucleotide sequence. The expression cassette may additionally contain selectable marker genes.

The expression cassette will include in the 5'-to-3' direction of transcription, a transcriptional and translational initiation region, a nucleotide sequence to be expressed, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences encoding 12-oxo-phytodienoate reductases and OYE homologues using heterologous promoters, the native promoter sequences may be used. Such constructs would change expression levels of 12-oxo-phytodienoate reductase or an OYE homologue in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of A. tumefaciens, such as the octopine synthase and nopaline synthase termination regions. See also Guerineau et al. (1991) Mol. Gen. Genet. 262:141–144; Proudfoot (1991) Cell 64:671–674; Sanfacon et al. (1991) Genes Dev. 5:141–149; Mogen et al. (1990) Plant Cell 2:1261–1272; Munroe et al. (1990) Gene 91:151–158; Ballas et al. (1989) Nucleic Acids Res. 17:7891–7903; and Joshi et al. (1987) Nucleic Acid Res. 15:9627–9639.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Where appropriate, the gene(s) may be optimized for increased expression in the transformed plant. That is, the genes can be synthesized using plant-preferred codons for improved expression. See, for example, Campbell and Gowri (1990) Plant Physiol. 92:1–11 for a discussion of host-preferred codon usage. Methods are available in the art for synthesizing plant-preferred genes. See, for example, U.S. Pat. Nos. 5,380,831, 5,436,391, and Murray et al. (1989) Nucleic Acids Res. 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) PNAS USA 86:6126–6130); potyvirus leaders, for example, TEV leader (Tobacco Etch Virus) (Allison et al. (1986); MDMV leader (Maize Dwarf Mosaic Virus); Virology 154:9–20), and human immunoglobulin heavy-chain binding protein (BiP), (Macejak et al. (1991) Nature 353:90–94); untranslated leader from the coat protein mRNA of alfalfa mosaic virus (AMV RNA 4) (Jobling et al. (1987) Nature 325:622–625); tobacco mosaic virus leader (TMV) (Gallie et al. (1989) in Molecular Biology of RNA, ed. Cech (Liss, New York), pp. 237–256); and maize chlorotic mottle virus leader (MCMV) (Lommel et al. (1991) Virology 81:382–385). See also, Della-Cioppa et al. (1987) Plant Physiol. 84:965–968. Other methods known to enhance translation can also be utilized, for example, introns, and the like.

A number of promoters can be used to drive the expression of coding sequences for enzymes involved in oxylipin synthesis. The promoters may be selected based on the desired timing, localization and level of expression of the 12-oxo-phytodienoate reductase or OYE genes in a plant. Constitutive, tissue-preferred, chemically regulatable, and pathogen-inducible and wound-inducible promoters can be used in the practice of the invention.

Such constitutive promoters include, for example, the core promoter of the Rsyn7 (copending U.S. application Ser. No. 08/661,601); the core CaMV 35S promoter (Odell et al. (1985) Nature 313:810–812); rice actin (McElroy et al. (1990) Plant Cell 2:163–171); ubiquitin (Christensen et al. (1989) Plant Mol. Biol. 12:619–632 and Christensen et al. (1992) Plant Mol. Biol. 18:675–689); pEMU (Last et al. (1991) Theor. Appl. Genet. 81:581–588); MAS (Velten et al. (1984) EMBO J. 3:2723–2730); ALS promoter (U.S. application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

For tissue-preferred expression, the nucleotide sequences of the invention can be operably linked to tissue-preferred promoters. Tissue-preferred promoters include Yamamoto et al. (1997) Plant J. 12(2)255–265; Kawamata et al. (1997) Plant Cell Physiol. 38(7):792–803; Hansen et al. (1997) Mol. Gen Genet. 254(3):337–343; Russell et al. (1997) Transgenic Res. 6(2):157–168; Rinehart et al. (1996) Plant Physiol. 112(3):1331–1341; Van Camp et al. (1996) Plant Physiol. 112(2):525–535; Canevascini et al. (1996) Plant Physiol. 112(2):513–524; Yamamoto et al. (1994) Plant Cell Physiol. 35(5):773–778; Lam (1994) Results Probl. Cell Differ. 20:181–196; Orozco et al. (1993) Plant Mol Biol. 23(6):1129–1138; Matsuoka et al. (1993) Proc Natl. Acad. Sci. USA 90(20):9586–9590; and Guevara-Garcia et al. (1993) Plant J. 4(3):495–505. Such promoters can be modified, if necessary, for weak expression.

Chemically regulatable promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemically regulatable promoters of interest include steroid-responsive promoters (see, for example, the glucocorticoid-inducible promoter in Schena et al. (1991) Proc. Natl. Acad. Sci. USA 88:10421–10425 and McNellis et al. (1998) Plant J. 14(2):247–257) and tetracycline-inducible and tetracycline-repressible promoters (see, for example, Gatz et al. (1991) Mol. Gen. Genet. 227:229–237, and U.S. Pat. Nos. 5,814,618 and 5,789,156), herein incorporated by reference.

Pathogen-inducible promoters can be used with control the expression of the 12-oxo-phytodienoate reductase or OYE genes of the invention. These promoters direct the expression of genes in plants following infection with one or more of the following pathogens including bacteria, fungi, viruses and nematodes. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol* 89:245–254; Uknes et al. (1992) *Plant Cell* 4:645–656; and Van Loon (1985) *Plant Mol. Virol.* 4:111–116. See also the copending applications entitled "Inducible Maize Promoters", U.S. Application Serial No. 60/076,100, filed Feb. 26, 1998, and U.S. Application Serial No. 60/079,648, filed Mar. 27, 1998, both of which are herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Wound-inducible promoters may be used in the constructions of the invention. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150); and the like, herein incorporated by reference.

Where low-level expression is desired, weak promoters will be used. Low-level expression of the OYE nucleotide sequences may be desired in methods of the invention requiring only minor changes in the level of an oxylipin, such as, for example jasmonic acid or methyl jasmonate. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 (copending U.S. application Ser. No. 08/661,601), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, copending application entitled "Constitutive Maize Promoters", U.S. Application Serial No. 60/076,075, filed Feb. 26, 1998, and herein incorporated by reference.

It is further recognized that the components of the expression cassette may be modified to increase expression. For example, truncated sequences, nucleotide substitutions or other modifications may be employed. See, for example Perlak et al. (1991) *Proc. Natl. Acad. Sci. USA* 88:3324–3328; Murray et al. (1989) *Nucleic Acid Research* 17:477–498; and WO 91/16432.

While 12-oxo-phytodienoate reductase is believed to be cytosolic, it is recognized that many enzymes involved in lipid metabolism in plants are present in chloroplasts and that it may be desirable to target the enzyme to this organelle. If necessary, the nucleotide sequence encoding a 12-oxo-phytodienoate reductase or OYE homologue of the invention, or any enzyme used in the methods of the invention, may be modified to direct the enzyme to the desired cellular compartment. Methods for modifying the coding sequence of an enzyme to target it to specific cellular compartments in a plant such as plastids, endoplasmic reticulum, dictyosomes, cytoplasm, mitochondria, microbodies, vacuoles and nuclei are known in the art. For certain enzymes, native targeting sequences may be removed or modified, and if desired, a new targeting sequence operably linked to the nucleotide sequence encoding the enzyme.

For example, it may be desirable to increase the level of a OYE homologue or 12-oxo-phytodienoate reductase in the chloroplast. Where the nucleic acid of interest is not directly inserted into the chloroplast, the expression cassette will additionally contain a nucleic acid encoding a transit peptide to direct the nucleic acid of interest to the chloroplasts. Such transit peptides are known in the art. See, for example, Von Heijne et al. (1991) *Plant Mol. Biol. Rep.* 9:104–126; Clark et al. (1989) *J. Biol. Chem.* 264:17544–17550; Della-Cioppa et al. (1987) *Plant Physiol.* 84:965–968; Romer et al. (1993) *Biochem. Biophys. Res. Commun.* 196:1414–1421; and Shah et al. (1986) *Science* 233:478–481.

Chloroplast-targeting sequences are known in the art and include the targeting sequences of the small subunit of ribulose-1,5-bisphosphate carboxylase (Rubisco) (de Castro Silva Filho et al. (1996) *Plant Mol. Biol.* 30:769–780; Schnell et al. (1991) *J. Biol. Chem.* 266(5):3335–3342); 5-(enolpyruvyl) shikimate-3-phosphate synthase (EPSPS) (Archer et al. (1990) *J. Bioenerg. Biomemb.* 22(6): 789–810); tryptophan synthase (Zhao et al. (1995) *J. Biol. Chem.* 270(11):6081–6087); plastocyanin (Lawrence et al. (1997) *J. Biol. Chem.* 272(33):20357–20363); chorismate synthase (Schmidt et al. (1993) *J. Biol. Chem.* 268(36): 27447–27457); and the light harvesting chlorophyll a/b binding protein (LHBP) (Lamppa et al. (1988) *J. Biol. Chem.* 263:14996–14999). See also Von Heijne et al. (1991) *Plant Mol. Biol. Rep.* 9:104–126; Clark et al. (1989) *J. Biol. Chem.* 264:17544–17550; Della-Cioppa et al. (1987) *Plant Physiol.* 84:965–968; Romer et al. (1993) *Biochem. Biophys. Res. Commun.* 196:1414–1421; and Shah et al. (1986) *Science* 233:478–481.

Alternatively, for expression of the nucleotide sequences of the invention in the chloroplast, the chloroplast can be transformed directly with the nucleotide sequences and expression cassettes of the invention. Methods for transformation of chloroplasts are known in the art. See, for example, Svab et al. (1990) *Proc. Natl. Acad. Sci. USA* 87:8526–8530; Svab and Maliga (1993) *Proc. Natl. Acad. Sci. USA* 90:913–917; Svab and Maliga (1993) *EMBO J.* 12:601–606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301–7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 10 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10: 143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

Alternatively, the sequences of the invention can be introduced into an organism and allowed to undergo recombination with homologous regions of the organism's genome. Such homologous recombination approaches are well known to those of ordinary skill in the art and can be used to stably incorporate sequences of the invention into an organism. Such approaches include, but are not limited to, chimeraplasty-based methods. Further, such approaches can be used to introduce "knockout mutations" into a specific gene of an organism that shares substantial homology to the sequences of the invention. A knockout mutation is any mutation in the sequence of a gene that eliminates or substantially reduces the function or the level of the product encoded by the gene. Methods involving transformation of an organism followed by homologous recombination to stably integrate the sequences of the invention into the genome organism are encompassed by the invention.

The present invention may be used for transformation of any plant species, including, but not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea spp.*), coconut (*Cocos nucifera*), pineapple (*Ananas comosus*), citrus trees (*Citrus spp.*), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (Saccharum spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

The modified plant may be grown into plants in accordance with conventional ways. See, for example, McCormick et al. (1986) *Plant Cell. Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The invention is drawn to compositions and methods for enhancing the resistance of a plant to biotic stress. Accordingly, the compositions and methods are also useful in increasing the resistance or tolerance of plants to stresses caused by organisms including, for examples fungi, bacteria, viruses, nematodes, insects and the like.

By "disease resistance" is intended that the plants avoid or reduce the disease symptoms that are the outcome of plant-pathogen interactions. That is, pathogens are prevented from causing plant diseases and the associated disease symptoms, or alternatively, the disease symptoms caused by the pathogen is minimized or lessened. The methods of the invention can be utilized to protect plants from disease, particularly those diseases that are caused by plant pathogens.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Plasmophora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis O, T* (*Cochliobolus heterostrophus*), *Helminthosporium carbonum I, II & III* (*Cochliobolus carbonum*), *Exserohilum turcicum I, II & III, Helminthosporium pedicellatum, Physoderma maydis, Phyllosticta maydis, Kabatiella-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora*, Corn stunt spiroplasma, *Diplodia macrospora, Sclerophthora macrospora, Peronosclerospora sorghi, Peronosclerospora philippinensis, Peronoscle-* rospora maydis, Peronosclerospora sacchari, Sphacelotheca reiliana, Physopella zeae, Cephalosporium maydis, Cephalosporium acremonium, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

Nematodes include parasitic nematodes such as root-knot, cyst, lesion, and reniform nematodes, etc.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; Melanotus spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipuncta*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentials*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

EXPERIMENTAL

EXAMPLE 1

Identification of Stress- and Pathogen-inducible Genes That Encode Plant Homologues of Old Yellow Enzyme To identify plant genes that are expressed in response to the initial oxidative burst that is associated with interaction between a resistant host plant and a pathogen, a maize suspension cell model system (Hi-II) was employed in this investigation. This cell suspension system was selected because, unlike intact plant tissues, it allows for the rapid treatment of a uniform population of cells with a equal dosage of a reagent. For a description of the Hi-II system, see Armstrong et al. (1991) *Maize Gen. Coop. Newsletter* 65:92–93. To mimic the oxidative burst associated with resistant plant-pathogen interactions, the cell suspension was treated with glucose and glucose oxidase for one hour to generate reactive oxygen species according to the method of Levine et al. (1994) *Cell* 70:583–593. Total RNA was isolated from the cell suspensions and analyzed using CuraGen Corporation's proprietary gene expression profiling process (GeneCalling®) as described in U.S. Pat. No. 5,871,697. A number of distinct transcripts increased in abundance following the oxidative burst and cDNAs corresponding to a portion of these transcripts of were cloned and sequenced. Interestingly, four of the transcripts that increased in relative abundance to the greatest extent corresponded to sequences encoding Old Yellow Enzyme (OYE) homologues in the Pioneer maize EST (expressed sequence tag) database. The increase in abundance of OYE transcripts in maize cell suspensions following an oxidative burst was confirmed by Northern blotting experiments (FIG. 1A).

Two full-length maize ESTs corresponding to the inducible OYE gene homologues were sequenced. ZmOYE1 (SEQ ID NO: 1) encodes a 375 amino acid protein (SEQ ID NO: 2). ZmOYE2 (SEQ ID NO: 3) encodes a 375 amino acid protein (SEQ ID NO: 4). The sequences of ZmOYE1 and ZmOYE2 are highly similar, sharing approximately 95% identity at both the nucleotide and amino acid levels. To determine the degree of similarity to the well-known yeast OYEs, ZmOYE1 (SEQ ID NO: 2) and ZmOYE2 (SEQ ID NO: 4) were aligned and compared with the amino acid sequences of OYE1 (SEQ ID NO: 6, GenBank Accession No. Q02899), OYE2 (SEQ ID NO: 7 GenBank Accession No. Q03558) and OYE3 (SEQ ID NO: 8, GenBank Accession No. P41816) using the BESTFIT algorithm (Wisconsin Genetics Software Package ,Version 10.0, Genetics Computer Group, Madison, Wis.) with default parameters. The results of the analysis are presented in Table 1. The amino acid sequences of ZmOYE1 and ZmOYE2 shared significant homologies to the yeast sequences. Similarly scores from comparisons of ZmOYE1 and ZmOYE2 and the yeast OYEs ranged from approximately 46 to 51 %, revealing that ZmOYE 1 and ZmOYE2 are OYE homologues. An analogous comparison of an Arabidopsis OYE (GenBank Accession No. Y10617) homologue yielded similarity scores of less than 40% (Schaller and Weiler (1997) *J. Biol. Chem.* 272:28066–28072). In view of these sequence comparisons, ZmOYE1 and ZmOYE2 are substantially more similar to the yeast OYEs than is the Arabidopsis OYE.

TABLE 1

Similarity Scores in Amino Acid Sequence Comparisons of ZmOYE1 and ZmOYE2 with yeast OYE1, OYE2 and OYE3

|  | OYEI (SEQ ID NO: 6) | OYE2 (SEQ ID NO: 7) | OYE3 (SEQ ID NO: 8) |
| --- | --- | --- | --- |
| ZmOYEI (SEQ ID NO: 2) | 46.13 | 49.58 | 50.70 |

TABLE 1-continued

Similarity Scores in Amino Acid Sequence Comparisons of ZmOYE1 and ZmOYE2 with yeast OYE1, OYE2 and OYE3

|  | OYEI (SEQ ID NO: 6) | OYE2 (SEQ ID NO: 7) | OYE3 (SEQ ID NO: 8) |
| --- | --- | --- | --- |
| ZmOYE2 (SEQ ID NO: 4) | 46.13 | 49.16 | 50.00 |

Further evidence that ZmOYE1 and ZmOYE2 are members of the OYE family comes from a more detailed analysis of the amino acid sequences. Amino acids that are critical for catalytic activity and are probably part of the active site of OYEs are conserved in the maize sequences. See Schaller and Weiler (1997) *J. Biol. Chem.* 272:28066–28072 for a detailed discussion of the amino acids that are critical for catalytic activity of OYEs.

The amino acid sequences ZmOYE1 (SEQ ID NO: 2) and ZmOYE2 (SEQ ID NO: 4) were aligned with amino acid sequences of OYE family members that were available in public databases using the CLUSTAL W multiple sequence alignment program (Version 1.74) (Thompson et al. (1994) *Nuc. Acids Res.* 22:4673–4680) with default parameters. The sequences include OYE1 from *Saccharomyces cerevisiae* (GenBank Accession No. Q02899); OYE2 from *Saccharomyces cerevisiae* (GenBank Accession No. Q03558), OYE3 from *Saccharomyces cerevisiae* (GenBank Accession No. P41816); KYE1 from *Kluyveromyces lactis* (GenBank Accession No. P40952); estrogen-binding protein (EBP1) from *Candida albicans* (GenBank Accession No. L25759); OYEA from *Schizosaccharomyces pombe* (GenBank Accession No. Q09670), OYEB from *Schizosaccharomyces pombe* (GenBank Accession No. Q09671); morphinone reductase (Morph-Red) from *Pseudomonas putida* (GenBank Accession No. U37350) and a 12-oxo-phytodienoate reductase from *Arabidopsis thaliana* (accession no. Y10617). The alignment revealed that the amino acid sequences of ZmOYE1 and ZmOYE2 share discrete regions of sequence identity with other OYE family members and overall, are highly similar to other OYEs.

While the physiological role of Old Yellow Enzyme in yeast remains elusive more than half a century after its discovery, an *Arabidopsis thaliana* homologue of this enzyme has been recently shown to possess 12-oxo-phytodienoate-10,11-reductase activity (Schaller and Weiler (1997) *J. Biol. Chem.* 272:28066–28072). As an enzyme in the branch of the oxylipin pathway extending from α-linolenic acid to jasmonic acid and methyl jasmonate, 12-oxo-phytodienoate reductase catalyzes the reduction of 12-oxo-phytodienoic acid to form 3-oxo-2-(2'-pentenyl)-cyclopentane-1-octanoic acid. Thus, in plants OYE homologues are likely to be involved in the synthesis of jasmonic acid and methyl jasmonate. Interestingly, OYE itself possesses 12-oxo-phytodienoate-10,11-reductase activity, suggesting that the primary physiological role of OYEs may be in oxylipin metabolism (Schaller and Weiler (1997) *J. Biol. Chem.* 272:28066–28072).

In plants, jasmonic acid and methyl jasmonate act as signal molecules in systemic wound responses and have been implicated as being involved in plants responses to osmotic stresses (Creelman et al. (1997) *Ann. Rev. Plant Physiol. Plant Mol. Biol.* 48:355–381). In addition, jasmonates have also been implicated as mediators of a variety of growth and developmental processes in plants, including fruit ripening, breaking seed dormancy, stomatal closure, production of viable pollen and leaf senescence, and inhibit other developmental processes including root growth, seed germination, embryogensis, flower bud formation and seedling growth (Parthier (1991) *Bot. Acta* 104:446–454).

Recent results indicate that jasmonates may also be involved in plant defense responses to pathogens. Local application of jasmonic acid to rice leaves resulted in systemic resistance to rice blast disease caused by infection with the fungus, *Magnaporthe grisea* (Herbert) Barr. (Schweizer et al. (1998) *Plant J.* 14:475–481). Furthermore, jasmonates appear to be a component of defense systems against pathogens that infect plant roots. Unlike wild-type plants which accumulate jasmonates, *Arabidopsis thaliana* triple mutants plants (fad3-2, fad7-2, fad8) that do not accumulate jasmonates are extremely susceptible to root rot caused by the fungal, root-pathogen *Pythium mastophorum* (Drechs.) (Vijayan et al. (1998) Proc. Natl. Acad. Sci. 95:7209–7214). Application of methyl jasmonate to the potting medium of the triple mutant plants greatly increased the resistance of these plants to root rot to near wild type levels. The incidence of root rot declined from greater than 90% in untreated mutant plants to less than 15% in the methyl jasmonate-treated plants. In addition, both coi1 and jar1 mutant *Arabidopsis thaliana* plants, which display reduced sensitivity to externally applied jasmonates, were significantly more susceptible to Pythium root rots than wild type plants (Vijayan et al. (1998) Proc. Natl. Acad. Sci. 95:7209–7214; Staswick et al. (1998) *Plant J.* 15:747–754). Unlike the fad triple mutant plants, the jasmonate-insensitive coi1 plants were still highly susceptible to root rot following an application of methyl jasmonate prior to inoculation with Pythium. These results with mutants impaired in jasmonate sensitivity further implicate jasmonates as necessary components of the defense system of *Arabidopsis thaliana* against Pythium root rots. Thus, there are now several independent lines of evidence to support a role for jasmonates as components of plant defense systems against pathogens.

EXAMPLE 2

Effects of Infection and Chitosan on ZmOYE Transcript Levels in Maize Suspension Cultures In view of the report that an Arabidopsis OYE is a 12-oxo-phytodienoate reductase (Schaller et al. (1997) *J. Biol. Chem.* 272:28066–28072), it is likely that the two newly discovered maize OYEs are 12-oxo-phytodienoate reductases. Because the levels of the transcripts encoding these putative maize 12-oxo-phytodienoate reductases increases following an oxidative burst, it is likely that these reductases act to mediate plant defense responses by catalyzing the synthesis of increased levels of jasmonic acid and methyl jasmonate synthesis in a plant following infection with a pathogen. Thus, further investigation of the expression of genes encoding these maize 12-oxo-phytodienoate reductases was initiated.

Figure 1B:
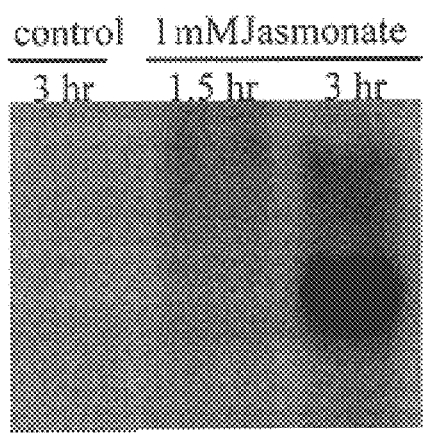
FIG. 1B depicts the effect of jasmonic acid on the level of ZmOYE transcripts in a maize suspension cultures. At the beginning of the experiment, jasmonic acid was added to the cultures to a level of 1 mM.

Because it is known that the expression of some of the other genes encoding enzymes in the same biosynthetic pathway as 12-oxo-phytodienoate reductase is induced by treatment of plants with jasmonic acid or methyl jasmonate, an experiment was conducted to investigate the effects of jasmonic acid on the expression of ZmOYE genes in maize cell suspensions. Cell suspension were treated with 1.0 mM JA and total RNA isolated at 0, 1.5 and 3 hours after treatment. At 3 hours after addition of jasmonic acid, a strong increase in ZmOYE transcript levels was detected (FIG. 1B).

Figure 2A:
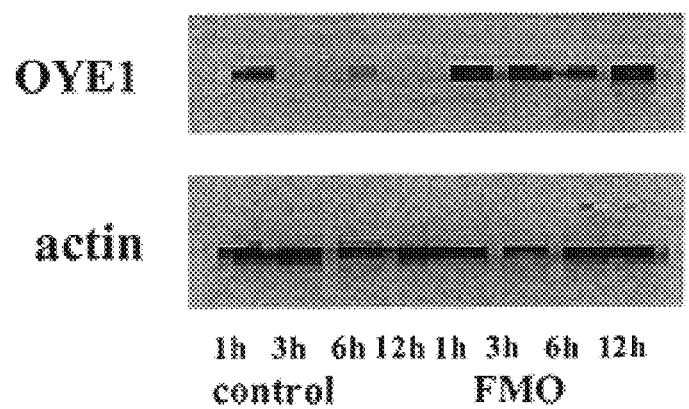
FIG. 2A: Northern blots to detect ZmOYE and actin transcripts.
Figure 2B:
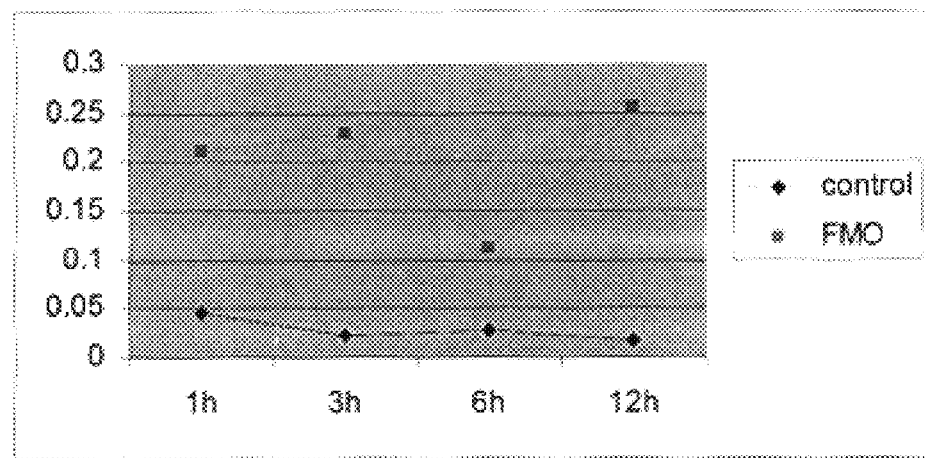
FIG. 2B: Graphical representation of ZmOYE transcript levels as detected by a Phosphoimager in cultures treated with spores of *Fusarium moniliforme* and control cultures.
Figure 3:
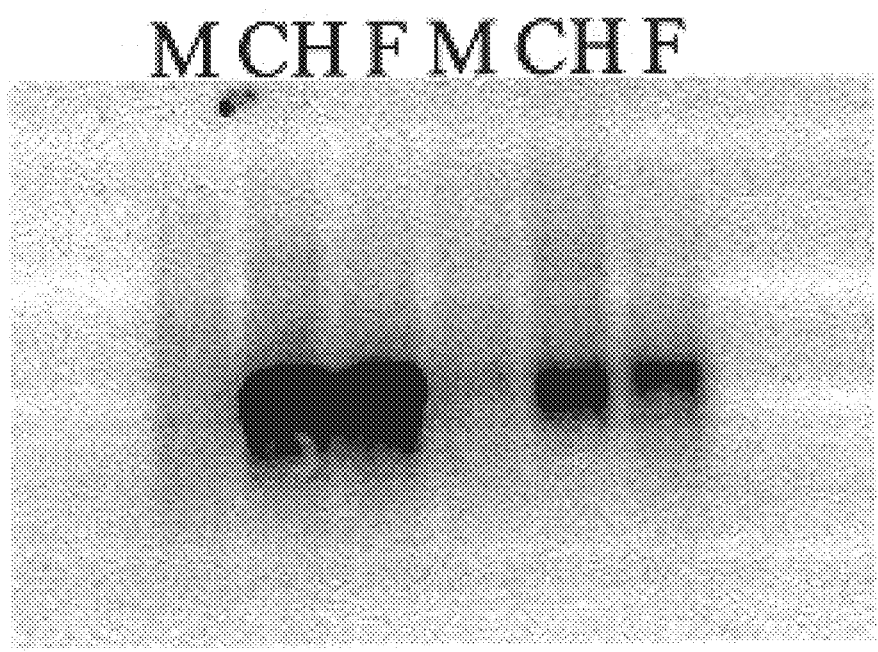
FIG. 3 depicts the results of a Northern blotting experiment to compare the effects of spores of *Fusarium moniliforme* and chitosan on the level of ZmOYE transcripts in maize suspension cultures.

Maize suspension cultures were also used to assess the effects of a pathogen on the expression of ZmOYE (FIG. 2). Spores of *Fusarium moniliforme* were added to maize suspension cultures and RNA was isolated at 1, 3, 6 and 12 hours after spore addition. RNA was also isolated from uninoculated cultures at the same time points. Northern blot analysis was conducted with a ZmOYE1 hybridization probe (FIG. 2A). As a loading control, the same filter was subsequently subjected to Northern blot analysis with an actin probe. A graphical representation of relative ZmOYE transcript levels for inoculated and control cultures is presented in FIG. 2B. At all time points, significantly higher transcript levels were detected in RNA isolated from the inoculated cultures than was detected in RNA isolated from the control cultures. Thus, ZmOYE genes are pathogen-inducible with increased expression detected as early as one hour after the addition of spores of a fungal pathogen. Furthermore, both the addition of spores of *Fusarium moniliforme* and the fungal elicitor, chitosan, were each separately able to dramatically increase the expression of OYE genes in maize suspension cultures (FIG. 3).

*F. moniliforme* is an important maize pathogen that causes stalk and kernel rot as well as seedling blight. In addition, toxins produced by this fungus are detrimental to mammals. Maize plants infected with *F. moniliforme*, but displaying no signs of disease, may still produce commercially unacceptable levels of the toxin. Thus, strategies for reducing the impact of *F. moniliforme* on maize are desired.

EXAMPLE 3

Effect of *Fusarium moniliforme* on ZmOYE Expression in Maize Silks

Unpollinated, fresh silks from maize plants of an inbred line, that is known to be resistant to ear mold caused by *Fusarium moniliforme*, were spray-inoculated with a solution comprising $10^6$ live *F. moniliforme* spores/mL. As a control, similar silks were sprayed with an equivalent volume of water. Following application of the spore-containing solution or water, the silks were covered with a tight-fitting plastic bag. The silks were harvested at six hours and one day after treatment. RNA was subsequently isolated from the silks and subjected to Northern blot analysis using a ZmOYE1 probe. As an RNA control, blots were also hybridized with an actin probe.

Figure 4:
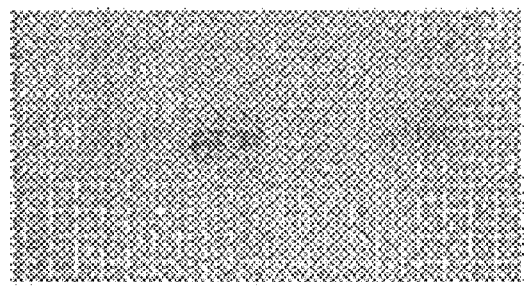
FIG. 4 depicts the results of a Northern blotting experiment to determine the effect of the treatment of unpollinated maize silks with spores of *Fusarium moniliforme* on the level of ZmOYE1 transcripts in the silks at six hours (6h) and one day (1d) after inoculation. RNA was isolated from inoculated (+) and control (−) silks and subjected to Northern blot analysis using a radiolabeled ZmOYE1 probe. As an RNA loading control, a Northern blot to detect actin transcripts was also conducted.
Figure 4:
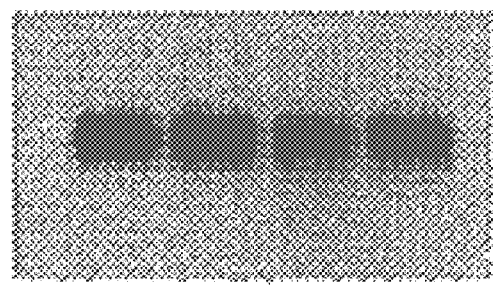

Similar to the results found in the undifferentiated maize suspension cells disclosed in Example 2, an increase in ZmOYE1 transcript levels was observed in differentiated plant tissues, silks, following inoculation with *F. moniliforme*. ZmOYE1 transcript levels were found to be increased in the silks of the earmold resistant plants within six hours after inoculation with the *F. moniliforme* spores, when compared to water-sprayed controls (FIG. 4). At one day after inoculation, ZmOYE1 transcript levels in the inoculated silks of the were still elevated above the level in the water-sprayed control silks. Actin transcript levels did not differ significantly with respect to treatment or time after inoculation (FIG. 4).

EXAMPLE 4

Isolation of a ZmOYE Promoter

The rapid increase in OYE transcript levels in maize suspension cultures following the addition of *F. moniliforme* spores indicates the ZmOYE genes, particularly the promoters, can be useful in engineering maize plants for enhanced resistance to diseases caused by *F. moniliforme*. Thus, a ZmOYE promoter was cloned from maize genomic DNA by a PCR method using a primer designed to anneal to a sequence within the 5'-untranslated region of the ZmOYE1 cDNA and Genome Walker reagents (Clontech Laboratories, Inc., Palo Alto, Calif.) according to the manufacturers' directions. The sequence of the ZmOYE promoter is set forth in SEQ ID NO: 5.

EXAMPLE 5

Identification of Four Additional ZmOYE genes in Maize

From a maize EST database, four ESTs corresponding to four additional genes that encode Old Yellow Enzyme (OYE) homologues were identified. Using standard methods, the corresponding full-length CDNA clones were partially sequenced. The new ZmOYE genes and their corresponding cDNA clones were designated ZmOYE3, ZmOYE4, ZmOYE5, and ZmOYE6. The nucleotide sequences the ZmOYE3, ZmOYE4, ZmOYE5, and ZmOYE6 cDNAs are set forth in SEQ ID NOS:6–9, respectively. The ZmOYE nucleotide sequences of the invention can be used to isolate the ZmOYE genes from maize using standard techniques known in the art, such as, for example, screening a maize genomic library or in the design of primers for the PCR amplification of maize genomic DNA.

EXAMPLE 6

Transformation and Regeneration of Transgenic Plants

Immature maize embryos from greenhouse donor plants are bombarded with a plasmid comprising an OYE homologue nucleotide sequence of the invention plus a plasmid containing the selectable marker gene PAT (Wohlleben et al. (1988) *Gene* 70:25–37) that confers resistance to the herbicide Bialaphos. Transformation is performed as follows. Media recipes follow below.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I H2O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H2O) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H2O after adjusting to pH 5.6); 3.0 g/l Gelrite (added after bringing to volume with D-I H2O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H2O), 0.1 g/l myo-inositol, and 40.0 g/l sucrose (brought to volume with polished D-I H2O after adjusting pH to 5.6); and 6 g/l bacto-agar (added after bringing to volume with polished D-I H2O), sterilized and cooled to 60° C.

Preparation of DNA

A plasmid vector comprising a OYE homologue nucleotide sequence operably linked to a promoter that drives expression in a plant is made. Alternatively, a plasmid vector comprising the ZmOYE promoter operably linked to a coding sequence of interest is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water

10 μl (1 μg) DNA in TrisEDTA buffer (1 μg total)

100 μl 2.5 M $CaCl_2$

10 μl 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for increased or decreased expression of OYE by measuring transcript levels, protein levels and/or 12-oxo-phytodienoate reductase activity levels.

EXAMPLE 7

Agrobacterium-mediated Transformation

For Agrobacterium-mediated transformation of maize with an OYE homologue nucleotide sequence of the invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the OYE homologue nucleotide sequence of interest to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated polynucleotide selected from the group consisting of:
   (a) a polynucleotide comprising the nucleotide sequence set forth in SEQ ID NO: 1;
   (b) a polynucleotide comprising a coding sequence for the amino acid sequence set forth in SEQ ID NO: 2; and
   (c) a polynucleotide comprising an antisense nucleotide sequence corresponding to the polynucleotide of (a) or (b).

2. An expression cassette comprising the polynucleotide of claim 1 operably linked to a promoter that drives expression in a plant cell.

3. The expression cassette of claim 2 wherein said promoter is selected from the group consisting of a constitutive promoter, a pathogen-inducible promoter, an insect-inducible promoter, a wound-inducible promoter, a stress-inducible promoter, a chemically regulatable promoter, a tissue-preferred promoter, and a developmentally regulated promoter.

4. The expression cassette of claim 1 wherein said promoter is operably linked to said nucleotide sequence for the production of antisense transcripts.

5. A transformed plant comprising in its genome at least one stably incorporated DNA construct comprising a nucleotide sequence operably linked to a promoter that drives expression in a plant cell, said nucleotide sequence selected from the group consisting of:
   (a) a polynucleotide comprising the nucleotide sequence set forth in SEQ ID NO: 1;
   (b) a polynucleotide comprising a coding sequence for the amino acid sequence set forth in SEQ ID NO: 2; and
   (c) a polynucleotide comprising an antisense nucleotide sequence corresponding to the poly nucleotide of (a) or (b).

6. The plant of claim 5 wherein said promoter is operably linked to said nucleotide sequence for the production of antisense transcripts.

7. The plant of claim 5 wherein said promoter is selected from the group consisting of a constitutive promoter, a pathogen-inducible promoter, an insect-inducible promoter, a wound-inducible promoter, a stress-inducible promoter, a chemically regulatable promoter, a tissue-preferred promoter, and a developmentally regulated promoter.

8. The plant of claim 5 wherein said plant is a monocot.

9. The plant of claim 8 wherein said monocot is selected from the group consisting of maize, wheat, rice, sorghum, barley, millet and rye.

10. Transformed seed of the plant of claim 5, wherein the seed comprises the DNA construct.

11. The plant of claim 5 wherein said plant is a dicot.

12. The plant of claim 11 wherein said dicot is selected from the group consisting of soybean, Brassica sp., alfalfa, safflower, sunflower, cotton and potato.

13. Transformed seed of the plant of any one of claims 6, 7, 8, 9, 11, and 12, wherein the seed comprises the DNA construct.

14. A transformed plant cell comprising in its genome at least one stably incorporated DNA construct comprising a nucleotide sequence operably linked to a promoter that drives expression in a plant cell, said nucleotide sequence selected from the group consisting of:

(a) a polynucleotide comprising the nucleotide sequence set forth in SEQ ID NO: 1;

(b) a polynucleotide comprising a coding sequence for the amino acid sequence set forth in SEQ ID NO: 2; and (c) a polynucleotide comprising an antisense nucleotide sequence corresponding to the polynucleotide of (a) or (b).

15. An isolated polynucleotide comprising at least 95% sequence identity to SEQ ID NO: 1, wherein said isolated polynucleotide encodes a polypeptide comprising 12-oxo-phytodienoate reductase activity, or is a complement of a nucleotide sequence that encodes said polypeptide.

16. An expression comprising the polynucleotide of claim 15 operably linked to a promoter that drives expression in a plant cell.

17. The expression cassette of claim 16 wherein said promoter is selected from the group consisting of a constitutive promoter, a pathogen-inducible promoter, an insect-inducible promoter, a wound-inducible promoter, a stress-inducible promoter, a chemically regulatable promoter, a tissue-preferred promoter, and a developmentally regulated promoter.

18. A transformed plant cell comprising in its genome at least one stably incorporated DNA construct comprising the polynucleotide of claim 15, said polynucleotide operably linked to a promoter that drives expression in a plant cell.

19. A transformed plant comprising in its genome at least one stably incorporated DNA construct comprising a nucleotide sequence operably linked to a promoter that drives expression in a plant cell, said nucleotide sequence comprising at least 95% sequence identity to SEQ ID NO: 1, wherein said isolated polynucleotide encodes a polypeptide comprising 12-oxo-phytodienoate reductase activity, or is a complement of a nucleotide sequence that encodes said polypeptide.

20. The plant of claim 19 wherein said promoter is selected from the group consisting of a constitutive promoter, a pathogen-inducible promoter, an insect-inducible promoter, a wound-inducible promoter, a stress-inducible promoter, a chemically regulatable promoter, a tissue-preferred promoter, and a developmentally regulated promoter.

21. The plant of claim 19 wherein said plant is a monocot.

22. The plant of claim 21 wherein said monocot is selected from the group consisting of maize, wheat, rice, sorghum, barley, millet and rye.

23. The plant of claim 19 wherein said plant is a dicot.

24. Transformed seed of the plant of claim 19, wherein the seed comprises the DNA construct.

* * * * *

UNITED STATES PATENT AND TRADEMARK OFFICE
CERTIFICATE OF CORRECTION

PATENT NO. : 6,515,202 B1  
DATED : February 4, 2003  
INVENTOR(S) : Crane et al.

It is certified that error appears in the above-identified patent and that said Letters Patent is hereby corrected as shown below:

Column 49,
Line 58, "claim 1" should read -- claim 2 --.

Column 50,
Line 40, "poly nucleotide" should read -- polynucleotide --.

Column 51,
Line 13, after "expression" insert -- cassette --.

Signed and Sealed this

Twenty-eighth Day of October, 2003

JAMES E. ROGAN  
*Director of the United States Patent and Trademark Office*